(12) United States Patent
Tomioka et al.

(10) Patent No.: US 11,600,102 B2
(45) Date of Patent: Mar. 7, 2023

(54) DETECTION DEVICE AND METHOD FOR MANUFACTURING THE SAME

(71) Applicant: Japan Display Inc., Tokyo (JP)

(72) Inventors: Yasushi Tomioka, Tokyo (JP); Kazuki Matsunaga, Tokyo (JP); Toshiyuki Higano, Tokyo (JP); Kazuhiro Nishiyama, Tokyo (JP)

(73) Assignee: Japan Display Inc., Tokyo (JP)

( * ) Notice: Subject to any disclaimer, the term of this patent is extended or adjusted under 35 U.S.C. 154(b) by 0 days.

(21) Appl. No.: 17/517,109

(22) Filed: Nov. 2, 2021

(65) Prior Publication Data

US 2022/0058365 A1 Feb. 24, 2022

Related U.S. Application Data

(63) Continuation of application No. PCT/JP2020/014905, filed on Mar. 31, 2020.

(30) Foreign Application Priority Data

May 8, 2019 (JP) .............................. JP2019-088396

(51) Int. Cl.
*G06V 40/13* (2022.01)
*H01L 27/146* (2006.01)

(52) U.S. Cl.
CPC ...... *G06V 40/1318* (2022.01); *G06V 40/1329* (2022.01); *H01L 27/14643* (2013.01); *H01L 27/14685* (2013.01)

(58) Field of Classification Search
None
See application file for complete search history.

(56) References Cited

U.S. PATENT DOCUMENTS 11,341,763 B2 * 5/2022 Kim .................... H01L 27/3225
2007/0253606 A1 * 11/2007 Higuchi ............. G06V 40/1318
382/124

(Continued)

FOREIGN PATENT DOCUMENTS

JP 2005-072662 A 3/2005
JP 2007-299084 A 11/2007

(Continued)

OTHER PUBLICATIONS

International Search Report issued in related International Patent Application No. PCT/JP2020/014905 dated Jun. 23, 2020 and English translation of same. 5 pages.

(Continued)

*Primary Examiner* — Joseph R Haley
(74) *Attorney, Agent, or Firm* — K&L Gates LLP

(57) ABSTRACT

According to an aspect, a detection device includes a plurality of light-receiving elements configured to receive light, and a light guide portion one surface of which faces the light-receiving elements. The light guide portion includes a plurality of light guide paths provided throughout from the one surface to the other surface of the light guide portion, and a light-absorbing portion having higher absorbance of the light than that of the light guide paths. When viewed from a direction in which the light-receiving elements and the light guide portion are stacked, more than one of the light guide paths overlap one of the light-receiving elements.

9 Claims, 18 Drawing Sheets

(56) References Cited

U.S. PATENT DOCUMENTS

| | | | |
|---|---|---|---|
| 2017/0220840 A1* | 8/2017 | Wickboldt | ............ G06F 1/1637 |
| 2018/0012069 A1 | 1/2018 | Chung et al. | |
| 2018/0366593 A1* | 12/2018 | Huang | .............. H01L 27/14623 |
| 2020/0259024 A1 | 8/2020 | Huang et al. | |
| 2020/0410201 A1* | 12/2020 | Nilsson | ................. G06F 3/0304 |
| 2021/0167229 A1* | 6/2021 | Lee | .................... H01L 27/1443 |

FOREIGN PATENT DOCUMENTS

| | | |
|---|---|---|
| JP | 2009-276976 A | 11/2009 |
| JP | 2019-003650 A | 1/2019 |

OTHER PUBLICATIONS

Written Opinion issued in related International Patent Application No. PCT/JP2020/014905 dated Jun. 23, 2020. 4 pages.
Office Action issued in related Japanese Patent Application No. 2019-088396 dated Jan. 4, 2023 and English translation of same. 6 pages.

\* cited by examiner

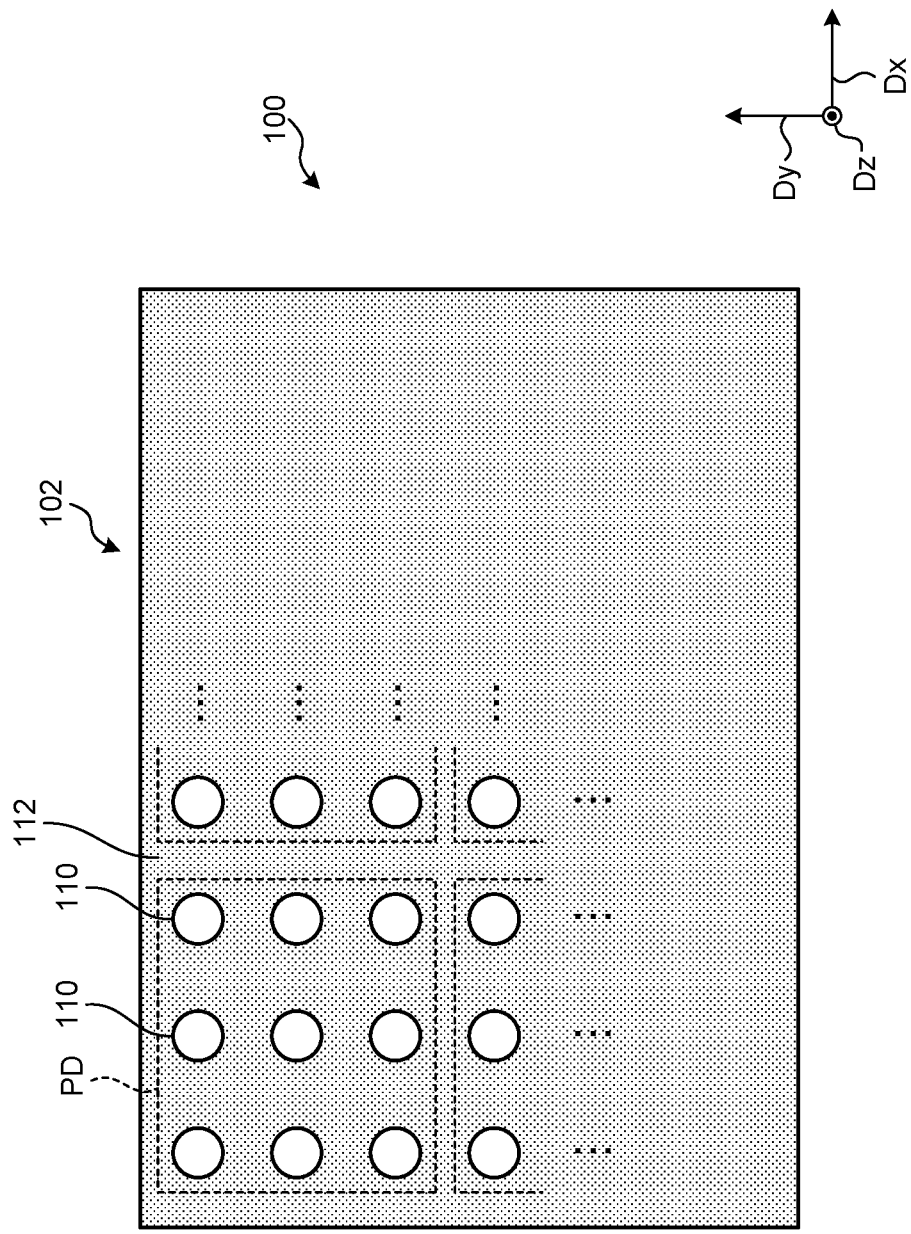

DETECTION DEVICE AND METHOD FOR MANUFACTURING THE SAME

CROSS-REFERENCE TO RELATED APPLICATION

This application claims the benefit of priority from Japanese Patent Application No. 2019-088396 filed on May 8, 2019 and International Patent Application No. PCT/JP2020/014905 filed on Mar. 31, 2020, the entire contents of which are incorporated herein by reference.

BACKGROUND

1. Technical Field

What is disclosed herein relates to a detection device and a method for manufacturing the same.

2. Description of the Related Art

In recent years, optical biosensors are known as biosensors used, for example, for personal authentication (for example, in United States Unexamined Patent Application Publication No. 2018/0012069). Such an optical biosensor includes a light-receiving element that changes a signal to be output therefrom depending on an amount of received light. In the biosensor described in United States Unexamined Patent Application Publication No. 2018/0012069, a plurality of such light-receiving elements, such as photodiodes, are arranged on a substrate.

An optical detection device including the biosensor needs to guide light to the light-receiving elements. The optical detection device leaves room for improvement to appropriately guide the light to the light-receiving elements.

For the foregoing reasons, there is a need for a detection device capable of appropriately guiding the light to the light-receiving elements, and a method for manufacturing the detection device.

SUMMARY

According to an aspect, a detection device includes: a plurality of light-receiving elements configured to receive light; and a light guide portion one surface of which faces the light-receiving elements. The light guide portion includes a plurality of light guide paths provided throughout from the one surface to the other surface of the light guide portion, and a light-absorbing portion having higher absorbance of the light than that of the light guide paths. When viewed from a direction in which the light-receiving elements and the light guide portion are stacked, more than one of the light guide paths overlap one of the light-receiving elements.

BRIEF DESCRIPTION OF THE DRAWINGS

FIG. 10 is another schematic diagram of the light guide body according to the first embodiment;

DETAILED DESCRIPTION

Figure 1:
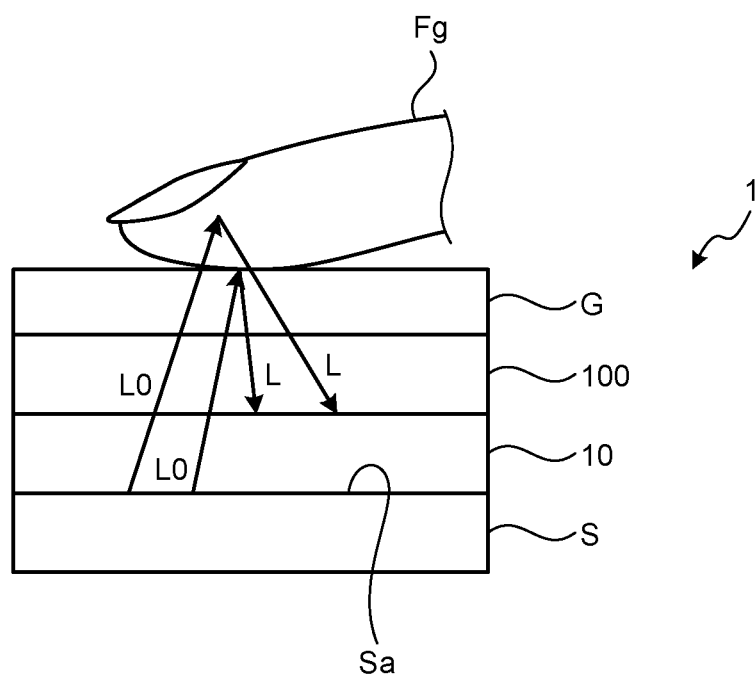
FIG. 1 is a schematic diagram illustrating a detection device according to a first embodiment.

The following describes the embodiments of the present invention with reference to the drawings. What is disclosed herein is merely an example, and the present invention naturally encompasses appropriate modifications easily conceivable by those skilled in the art while maintaining the gist of the invention. To further clarify the description, the drawings schematically illustrate, for example, widths, thicknesses, and shapes of various parts as compared with actual aspects thereof, in some cases. However, they are merely examples, and interpretation of the present invention is not limited thereto. The same element as that illustrated in a drawing that has already been discussed is denoted by the same reference numeral through the description and the drawings, and detailed description thereof will not be repeated in some cases where appropriate.

First Embodiment (Overall Configuration of Detection Device)

FIG. 1 is a schematic diagram illustrating a detection device according to a first embodiment. A detection device 1 according to a first embodiment is a device that receives light L to detect information. In the present embodiment, the detection device 1 detects biological information on a user. As illustrated in FIG. 1, the detection device 1 includes a light source S, a sensor 10, a light guide body 100, and a cover glass G. The light source S, the sensor 10, the light guide body 100, and the cover glass G are stacked in the order as listed.

The light source S has a light-emitting surface Sa for emitting light to emit light L0 from the light-emitting surface Sa toward the sensor 10. The light source S is a backlight. The light source S may include, as light source elements, for example, light-emitting diodes (LEDs) for emitting light in a predetermined color. The light source S may be, for example, what is called a side light-type backlight that includes a light guide plate provided at a location corresponding to the sensor 10 and a plurality of light source elements arrayed at one end or both ends of the light guide plate. The light source S may be what is called a direct-type backlight that includes the light source elements (such as the LEDs) provided directly below the sensor 10. The light source S is not limited to the backlight and may be provided on a lateral side or an upper side of the sensor 10, and may emit the light L0 from the lateral side or the upper side of a finger Fg of the user. That is, the light source S may be provided on a detection target object (finger Fg) side, not on the light guide body 100 side. The light source S need not be provided if natural light is used as the light L.

The sensor 10 is provided so as to face the light-emitting surface Sa of the light source S. The light L0 emitted from the light source S passes through the sensor 10, the light guide body 100, and the cover glass G. The sensor 10 is, for example, a light reflective biological information sensor and can detect asperities (such as a fingerprint) on a surface of the finger Fg or a palm of the user by detecting the light L serving as reflected light of the light L0. The sensor 10 may detect a vascular pattern or detect other biological information by detecting the light L reflected in the finger Fg or the palm. The wavelength of the light L from the light source S may be varied depending on the detection target object. For example, the light L0 of the visible light can be emitted from the light source S in the case of the fingerprint detection, and the light L0 of the near-infrared light can be emitted from the light source S in the case of the vascular pattern detection. The visible light is light of a wavelength band in a visible light range. The near-infrared light is light of a wavelength band in a near-infrared range and is light of a wavelength band from 700 nm to 950 nm, for example.

The light guide body 100 is provided on the detection target object (finger Fg) side of the sensor 10 and faces the sensor 10. The light guide body 100 is an optical element for guiding the light L to the sensor 10. A configuration of the light guide body 100 will be described later.

The cover glass G is a member for protecting the sensor 10 and the light source S and covers the light guide body 100, the sensor 10, and the light source S. The cover glass G is, for example, a glass substrate. The cover glass G is not limited to the glass substrate and may be, for example, a resin substrate. The cover glass G may not be provided.

The detection device 1 may be provided with a display panel instead of the light source S. The display panel may be, for example, an organic electroluminescent (EL) (organic light-emitting diode (OLED)) display panel or an inorganic EL (μ-LED or mini-LED) display panel. Alternatively, the display panel may be a liquid crystal display (LCD) panel that uses liquid crystal elements as display elements, or an electrophoretic display (EPD) panel that uses electrophoretic elements as the display elements. Even in this case, display light emitted from the display panel passes through the sensor 10, and the biological information on the user can be detected based on the light L reflected by the finger Fg.

(Sensor)

Figure 2:
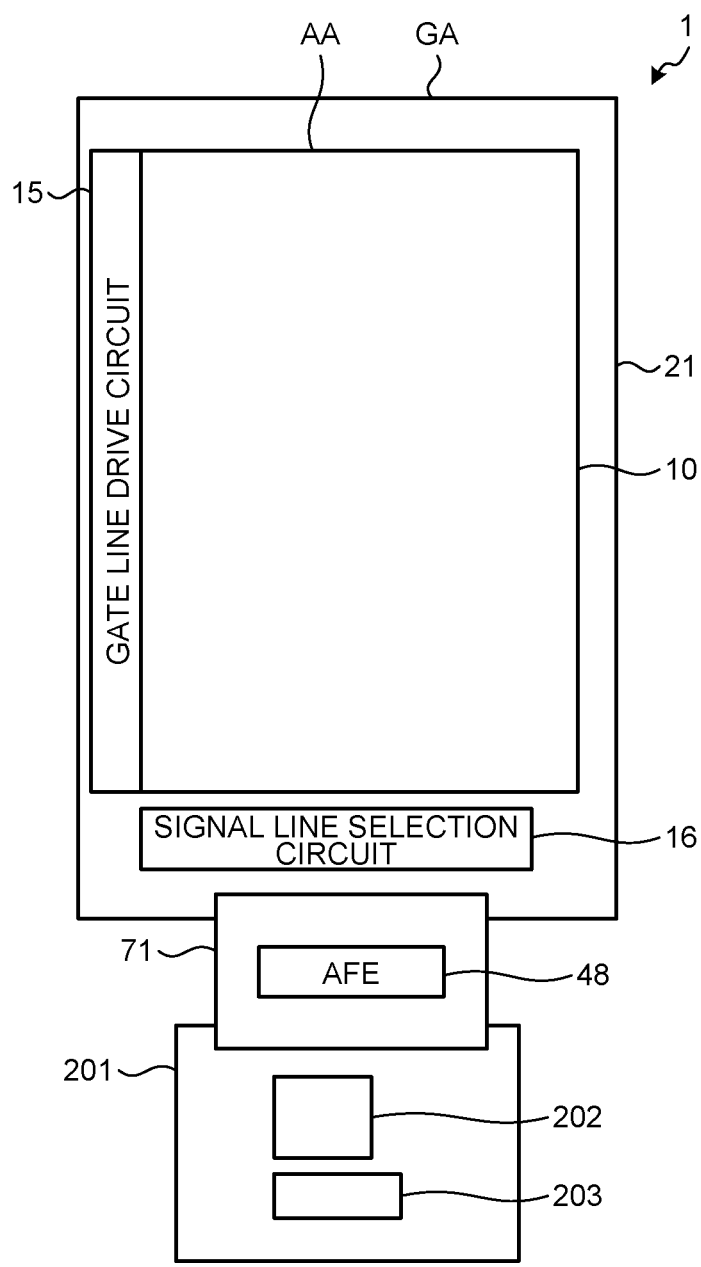
FIG. 2 is a plan view of the detection device including a sensor.
Figure 3:
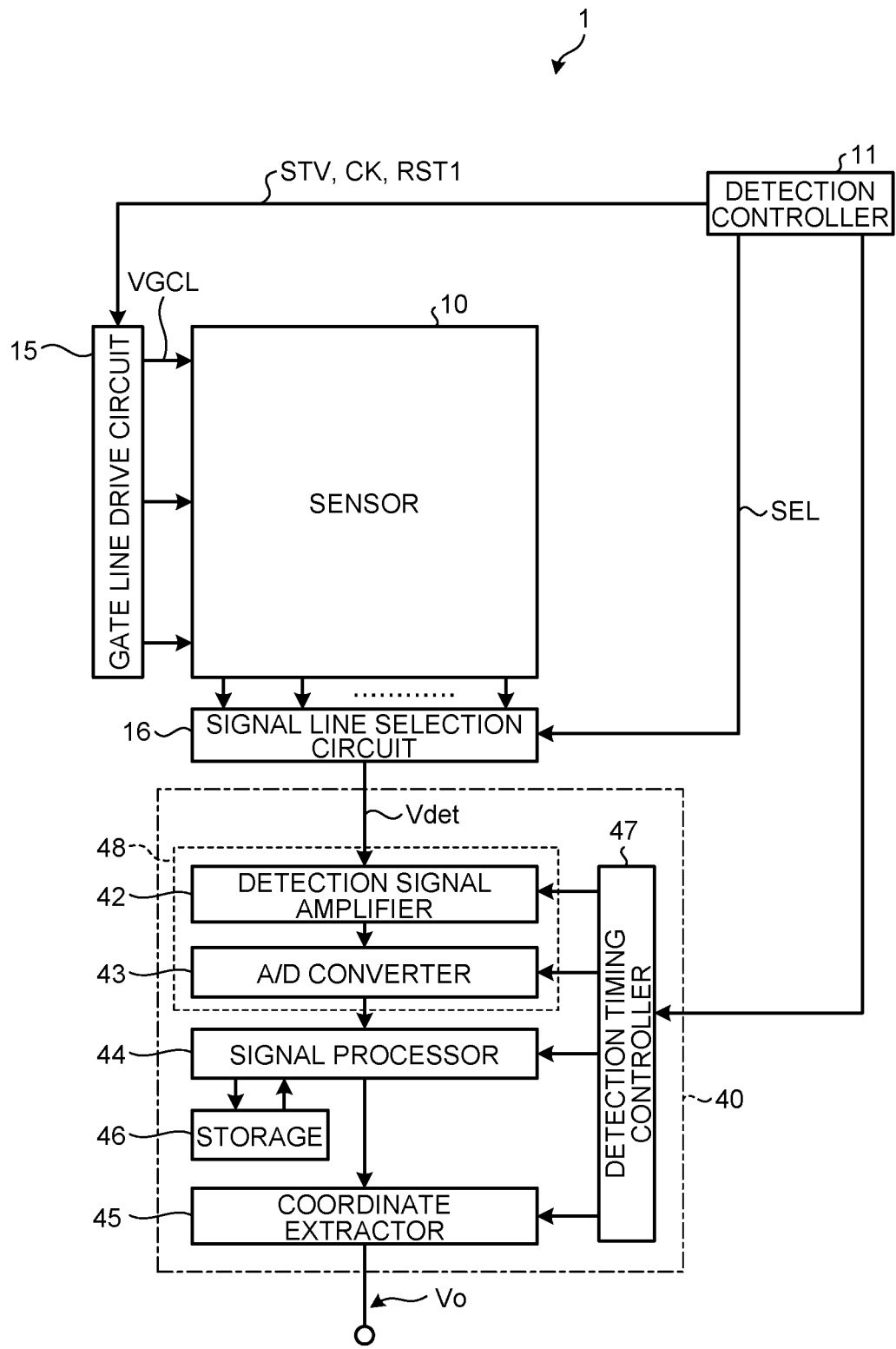
FIG. 3 is a block diagram illustrating a configuration example of the detection device including the sensor.

The following describes the sensor 10. FIG. 2 is a plan view of the detection device including the sensor. FIG. 3 is a block diagram illustrating a configuration example of the detection device including the sensor. As illustrated in FIG. 2, the detection device 1 includes an insulating substrate 21, the sensor 10, a gate line drive circuit 15, a signal line selection circuit 16, an analog front-end circuit (hereinafter, referred to as AFE) 48, a control circuit 202, and a power supply circuit 203.

As illustrated in FIG. 2, a control board 201 is electrically coupled to the insulating substrate 21 through a flexible printed circuit board 71. The flexible printed circuit board 71 is provided with the AFE 48. The control board 201 is provided with the control circuit 202 and the power supply circuit 203. The control circuit 202 is, for example, a field programmable gate array (FPGA). The control circuit 202 supplies control signals to the sensor 10, the gate line drive circuit 15, and the signal line selection circuit 16 to control a detection operation of the sensor 10. The power supply circuit 203 supplies voltage signals including, for example, a power supply signal SVS (refer to FIG. 5), to the sensor 10 and the gate line drive circuit 15.

As illustrated in FIG. 2, the insulating substrate 21 has a detection area AA and a peripheral area GA. The detection area AA is an area overlapping a plurality of light-receiving elements PD (refer to FIG. 5) included in the sensor 10. The peripheral area GA is an area outside the detection area AA and is an area not overlapping the light-receiving elements PD. The gate line drive circuit 15 and the signal line selection circuit 16 are provided in the peripheral area GA.

As illustrated in FIG. 3, the detection device 1 further includes a detection controller 11 and a detector 40. The control circuit 202 includes some or all functions of the detection controller 11. The control circuit 202 also includes some or all functions of the detector 40 except those of the AFE 48.

The sensor 10 is an optical sensor including the light-receiving elements PD each serving as a photoelectric conversion element. Each of the light-receiving elements PD is the photoelectric conversion element, more specifically, a photodiode, and outputs an electrical signal corresponding to the received light as a detection signal Vdet to the signal line selection circuit 16. The sensor 10 performs the detection in response to a gate drive signal VGCL supplied from the gate line drive circuit 15.

The detection controller 11 is a circuit that supplies respective control signals to the gate line drive circuit 15, the signal line selection circuit 16, and the detector 40 to control operations thereof. The detection controller 11 supplies various control signals including, for example, a start signal STV, a clock signal CK, and a reset signal RST1 to the gate line drive circuit 15. The detection controller 11 also supplies various control signals including, for example, a selection signal SEL to the signal line selection circuit 16.

The gate line drive circuit 15 is a circuit that drives a plurality of gate lines GCL (refer to FIG. 4) based on the various control signals. The gate line drive circuit 15 sequentially or simultaneously selects the gate lines GCL, and supplies the gate drive signals VGCL to the selected gate lines GCL. Through this operation, the gate line drive circuit 15 selects the light-receiving elements PD coupled to the gate lines GCL.

Figure 4:
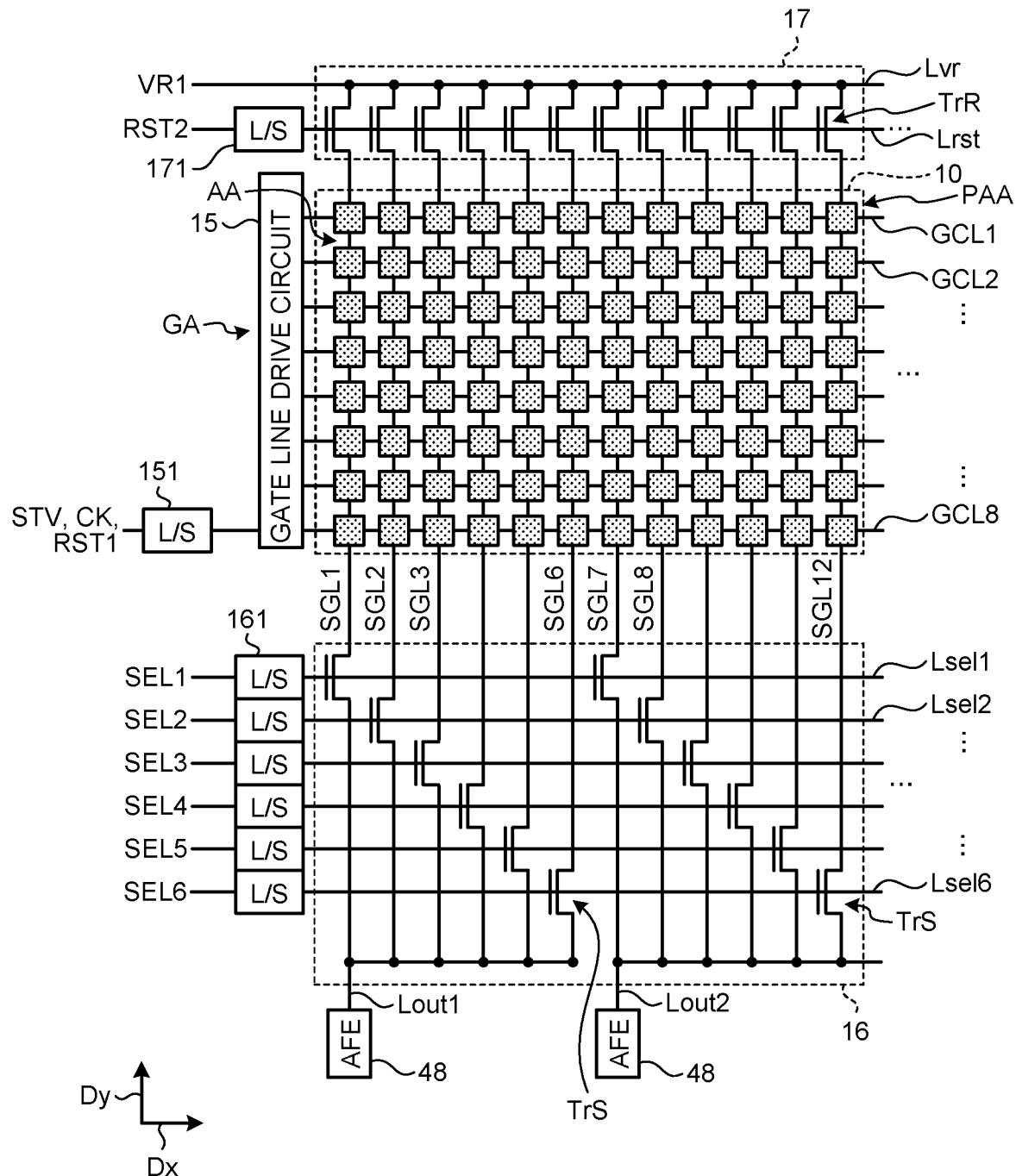
FIG. 4 is a circuit diagram illustrating the detection device.

The signal line selection circuit 16 is a switch circuit that sequentially or simultaneously selects a plurality of signal lines SGL (refer to FIG. 4). The signal line selection circuit 16 couples the selected signal lines SGL to the AFE 48 based on the selection signal SEL supplied from the detection controller 11. Through this operation, the signal line selection circuit 16 outputs the detection signal Vdet of each of the light-receiving elements PD to the detector 40.

The detector 40 includes the AFE 48, a signal processor 44, a coordinate extractor 45, a storage 46, and a detection timing controller 47. The detection timing controller 47 controls the AFE 48, the signal processor 44, and the coordinate extractor 45 based on a control signal supplied from the detection controller 11 such that they operate in synchronization with one another.

The AFE 48 is a signal processing circuit having functions of at least a detection signal amplifier 42 and an analog-to-digital (A/D) converter 43. The detection signal amplifier 42 amplifies the detection signal Vdet. The A/D converter 43 converts an analog signal output from the detection signal amplifier 42 into a digital signal.

The signal processor 44 is a logic circuit that detects, based on an output signal of the AFE 48, a predetermined physical quantity input to the sensor 10. When a finger is in contact with or in proximity to a detection surface, the signal processor 44 can detect the biological information based on the signal from the AFE 48.

The storage 46 temporarily stores a signal calculated by the signal processor 44. The storage 46 may be, for example, a random-access memory (RAM) or a register circuit.

The coordinate extractor 45 is a logic circuit that obtains detected coordinates such as the asperities of the surface of, for example, the finger when the contact or the proximity of the finger is detected by the signal processor 44. The coordinate extractor 45 combines the detection signals Vdet output from the light-receiving elements PD of the sensor 10 to generate two-dimensional information representing a shape such as the asperities of the surface of, for example, the finger. The coordinate extractor 45 may output the detection signals Vdet as sensor outputs Vo, without calculating the detected coordinates.

Figure 5:
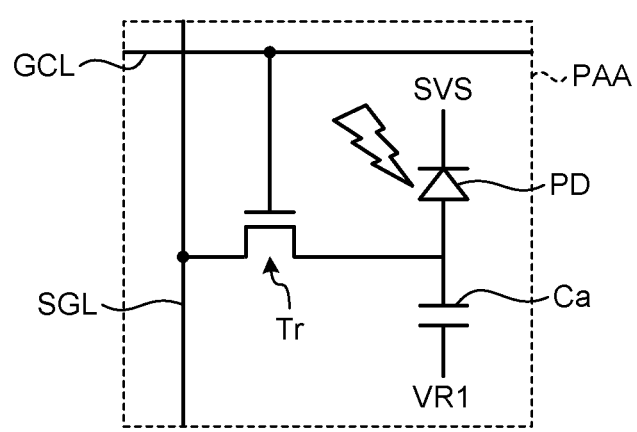
FIG. 5 is a circuit diagram illustrating a partial detection area.
Figure 6:
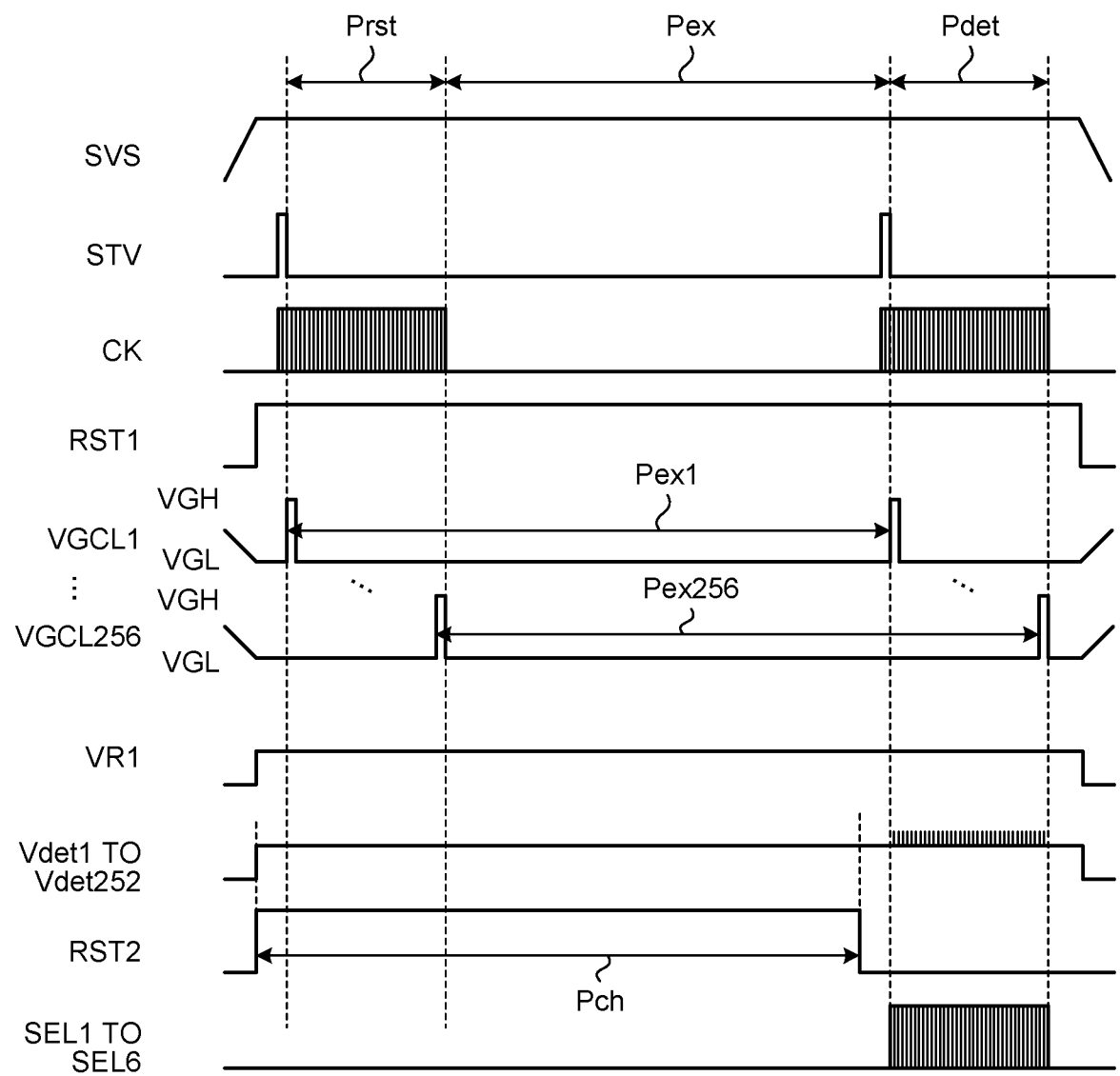
FIG. 6 is a timing waveform diagram illustrating an operation example of the detection device.

The following describes a circuit configuration example and an operation example of the detection device 1. FIG. 4 is a circuit diagram illustrating the detection device. FIG. 5 is a circuit diagram illustrating a partial detection area. FIG. 6 is a timing waveform diagram illustrating the operation example of the detection device.

As illustrated in FIG. 4, the sensor 10 has a plurality of partial detection areas PAA arranged in a matrix having a row-column configuration. As illustrated in FIG. 5, each of the partial detection areas PAA includes the light-receiving element PD, a capacitive element Ca, and a first switching element Tr. The first switching element Tr is provided corresponding to the light-receiving element PD. The first switching element Tr includes a thin-film transistor. In this example, the first switching element Tr includes an n-channel metal oxide semiconductor (MOS) thin-film transistor (TFT). The gate of the first switching element Tr is coupled to each of the gate lines GCL. The source of the first switching element Tr is coupled to each of the signal lines SGL. The drain of the first switching element Tr is coupled to the anode of the light-receiving element PD and the capacitive element Ca.

The cathode of the light-receiving element PD is supplied with the power supply signal SVS from the power supply circuit 203. The capacitive element Ca is supplied with a reference signal VR1 serving as an initial potential of the capacitive element Ca from the power supply circuit 203.

When the partial detection area PAA is irradiated with light, a current corresponding to an amount of the light flows through the light-receiving element PD. As a result, an electrical charge is stored in the capacitive element Ca. After the first switching element Tr is turned on, a current corresponding to the electrical charge stored in the capacitive element Ca flows through the signal line SGL. The signal line SGL is coupled to the AFE 48 through the signal line selection circuit 16. Thus, the detection device 1 can detect a signal corresponding to the amount of the light emitted to the light-receiving element PD for each of the partial detection areas PAA.

As illustrated in FIG. 4, the gate lines GCL extend in a first direction Dx and are coupled to the partial detection areas PAA arranged in the first direction Dx. A plurality of gate lines GCL1, GCL2, ..., GCL8 are arranged in a second direction Dy and are each coupled to the gate line drive circuit 15. In the following description, the gate lines GCL1, GCL2, ..., GCL8 will each be simply referred to as the gate line GCL when they need not be distinguished from one another. Although the number of the gate lines GCL is eight, this is merely an example. Eight or more, such as 256, of the gate lines GCL may be arranged.

The first direction Dx is a direction in a plane parallel to the insulating substrate 21, and is, for example, a direction parallel to the gate lines GCL. The second direction Dy is a direction in a plane parallel to the insulating substrate 21 and is a direction orthogonal to the first direction Dx. The second direction Dy may intersect the first direction Dx without being orthogonal thereto. A third direction Dz refers to a direction orthogonal to the first direction Dx and the second direction Dy. The third direction Dz is a direction orthogonal to the plane parallel to the insulating substrate 21.

The signal lines SGL extend in the second direction Dy and are coupled to the partial detection areas PAA arranged in the second direction Dy. A plurality of signal lines SGL1, SGL2, ..., SGL12 are arranged in the first direction Dx and are each coupled to the signal line selection circuit 16 and a reset circuit 17. Although the number of the signal lines SGL is 12, this is merely an example. Twelve or more, such as 252, of the signal lines SGL may be arranged. In FIG. 4, the sensor 10 is provided between the signal line selection circuit 16 and the reset circuit 17. The present embodiment is not limited thereto. The signal line selection circuit 16 and the reset circuit 17 may be coupled to the same ends of the signal lines SGL.

The gate line drive circuit 15 receives the various control signals such as the start signal STV, the clock signal CK, and a reset signal RST1 through a level shifter 151. The gate line drive circuit 15 includes a plurality of second switching elements TrG (refer to FIG. 8) and a shift register (not illustrated). By operations of the shift register and the second switching elements TrG, the gate line drive circuit 15 sequentially selects the gate lines GCL1, GCL2, ..., GCL8 in a time-division manner. The gate line drive circuit 15 supplies the gate drive signals VGCL to the first switching elements Tr through the selected gate lines GCL. With this operation, the partial detection areas PAA arranged in the first direction Dx are selected as detection target objects.

The signal line selection circuit 16 includes a plurality of selection signal lines Lsel, a plurality of output signal lines Lout, and third switching elements TrS. The third switching elements TrS are provided corresponding to the signal lines SGL. Six signal lines SGL1, SGL2, ..., SGL6 are coupled to a common output signal line Lout1. Six signal lines SGL7, SGL8, ..., SGL12 are coupled to a common output signal line Lout2. The output signal lines Lout1 and Lout2 are each coupled to the AFE 48.

The signal lines SGL1, SGL2, ..., SGL6 are grouped into a first signal line block, and the signal lines SGL7, SGL8, ..., SGL12 are grouped into a second signal line block. The selection signal lines Lsel are coupled to the gates of the respective third switching elements TrS included in one of the signal line blocks. One of the selection signal lines Lsel is coupled to the gates of the third switching elements TrS in the signal line blocks. Specifically, selection signal lines Lsel1, Lsel2, ..., Lsel6 are coupled to the third switching elements TrS corresponding to the signal lines SGL1, SGL2, ..., SGL6. The selection signal line Lsel1 is coupled to the third switching element TrS corresponding to the signal line SGL1 and the third switching element TrS corresponding to the signal line SGL7. The selection signal line Lsel2 is coupled to the third switching element TrS corresponding to the signal line SGL2 and the third switching element TrS corresponding to the signal line SGL8.

The control circuit 202 (refer to FIG. 2) sequentially supplies the selection signals SEL to the selection signal lines Lsel through level shifters 161. This operation causes the signal line selection circuit 16 to operate the third switching elements TrS to sequentially select the signal lines SGL in each of the signal line blocks in a time-division manner. The signal line selection circuit 16 simultaneously selects one signal line SGL in each of the signal line blocks. With the above-described configuration, the detection device 1 can reduce the number of integrated circuits (ICs) including the AFE 48 or the number of terminals of the ICs.

As illustrated in FIG. 4, the reset circuit 17 includes a reference signal line Lvr, a reset signal line Lrst, and fourth switching elements TrR. The fourth switching elements TrR are provided corresponding to the signal lines SGL. The reference signal line Lvr is coupled to either the sources or the drains of the fourth switching elements TrR. The reset signal line Lrst is coupled to the gates of the fourth switching elements TrR.

The control circuit 202 supplies a reset signal RST2 to the reset signal line Lrst through a level shifter 171. This operation turns on the fourth switching elements TrR to electrically couple the signal lines SGL to the reference signal line Lvr. The power supply circuit 203 supplies the reference signal VR1 to the reference signal line Lvr. This operation supplies the reference signal VR1 to the capacitive elements Ca included in the partial detection areas PAA.

As illustrated in FIG. 6, the detection device 1 includes a reset period Prst, an exposure period Pex, and a reading period Pdet. The power supply circuit 203 supplies the power supply signal SVS to the cathode of the light-receiving element PD through the reset period Prst, the exposure period Pex, and the reading period Pdet. At a time before the reset period Prst starts, the control circuit 202 supplies the reference signal VR1 and the reset signal RST2 serving as high-level voltage signals to the reset circuit 17. The control circuit 202 supplies the start signal STV to the gate line drive circuit 15 to start the reset period Prst.

During the reset period Prst, the shift register included in the gate line drive circuit 15 sequentially selects each of the gate lines GCL based on the start signal STV, the clock signal CK, and the reset signal RST1. The gate line drive circuit 15 sequentially supplies the gate drive signals VGCL to the gate lines GCL. The gate drive signal VGCL has a pulsed waveform having a high-level voltage VGH and a low-level voltage VGL. In FIG. 6, 256 gate lines GCL are provided, and the respective gate lines GCL are sequentially supplied with gate drive signals VGCL1, ..., VGCL256.

Thus, during the reset period Prst, the capacitive elements Ca of all the partial detection areas PAA are sequentially electrically coupled to the signal lines SGL and are supplied with the reference signal VR1. As a result, capacitances of the capacitive elements Ca are reset.

The exposure period Pex starts after the gate drive signal VGCL256 is supplied to the gate line GCL. The actual exposure periods Pex1, ..., Pex256 in the partial detection areas PAA corresponding to the gate lines GCL differ from one another in start timing and end timing. Each of the exposure periods Pex1, ..., Pex256 starts at a time when the gate drive signal VGCL changes from the high-level voltage VGH to the low-level voltage VGL during the reset period Prst. Each of the exposure periods Pex1, ..., Pex256 ends at a time when the gate drive signal VGCL changes from the low-level voltage VGL to the high-level voltage VGH during the reading period Pdet. The lengths of exposure time of the exposure periods Pex1, ..., Pex256 are equal.

During the exposure period Pex, the current corresponding to the light emitted to the light-receiving element PD flows in each of the partial detection areas PAA. As a result, the electrical charge is stored in each of the capacitive elements Ca.

At a time before the reading period Pdet starts, the control circuit 202 sets the reset signal RST2 to a low-level voltage. This operation stops the operation of the reset circuit 17. During the reading period Pdet, the gate line drive circuit 15 sequentially supplies the gate drive signals VGCL1, ..., VGCL256 to the gate lines GCL in the same manner as during the reset period Prst.

For example, during a period in which the gate drive signal VGCL1 is at the high-level voltage VGH, the control circuit 202 sequentially supplies selection signals SEL1, ..., SEL6 to the signal line selection circuit 16. With this operation, the signal lines SGL for the partial detection areas PAA selected by the gate drive signal VGCL1 are sequentially or simultaneously coupled to the AFE 48. As a result, the detection signal Vdet is supplied to the AFE 48. In the same manner, the signal line selection circuit 16 sequentially selects the signal line SGL in each period in which a corresponding one of the gate drive signals VGCL is set to the high-level voltage VGH. Thus, the detection device 1 can output the detection signals Vdet of all the partial detection areas PAA to the AFE 48 during the reading period Pdet.

The detection device 1 may perform the fingerprint detection by repeatedly performing the processing during the reset period Prst, the exposure period Pex, and the reading period Pdet. Alternatively, the detection device 1 may start the detection operation when having detected that a finger, for example, is in contact with or in proximity to the detection surface.

Figure 7:
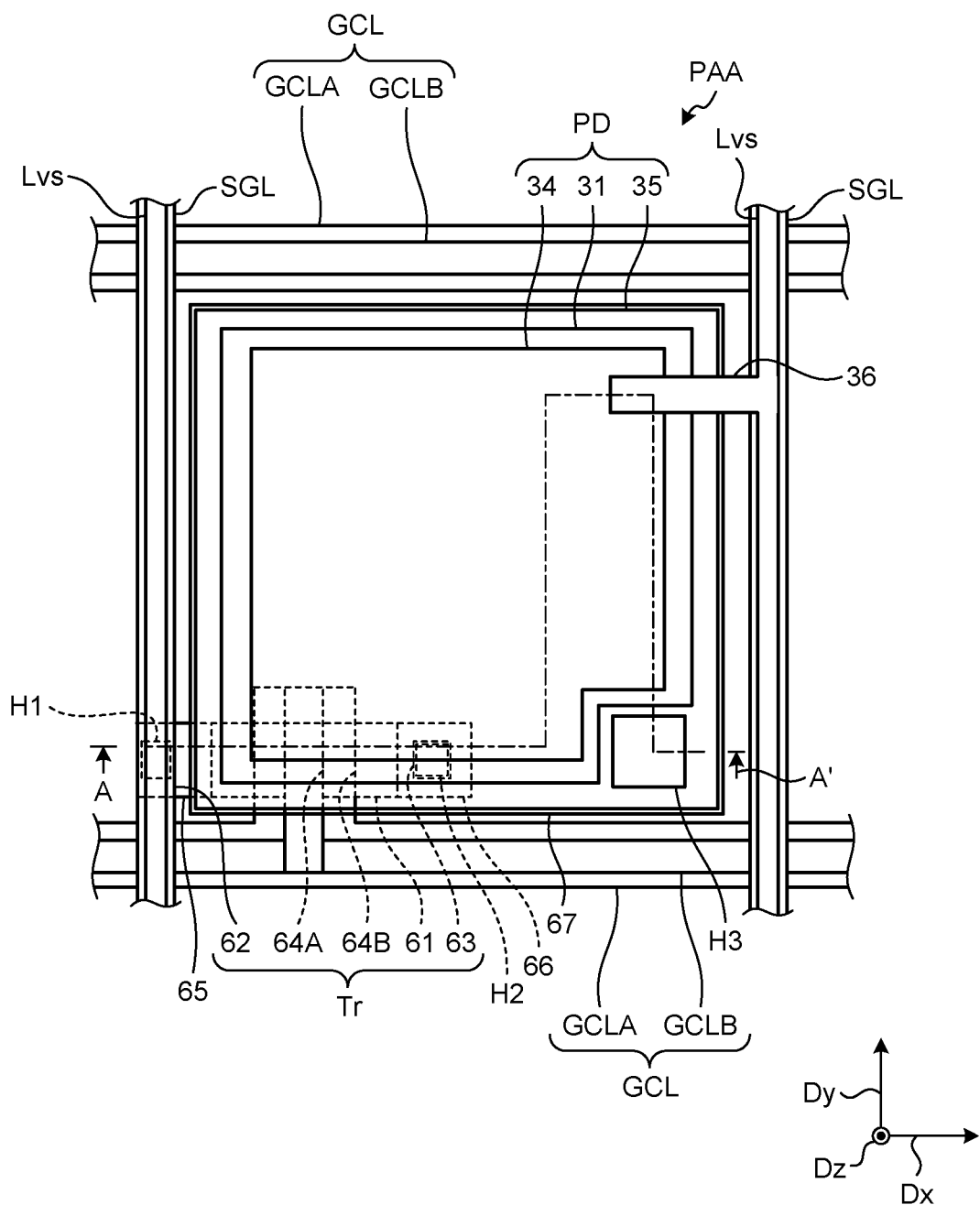
FIG. 7 is a plan view schematically illustrating the partial detection area of the detection device according to the first embodiment.
Figure 8:
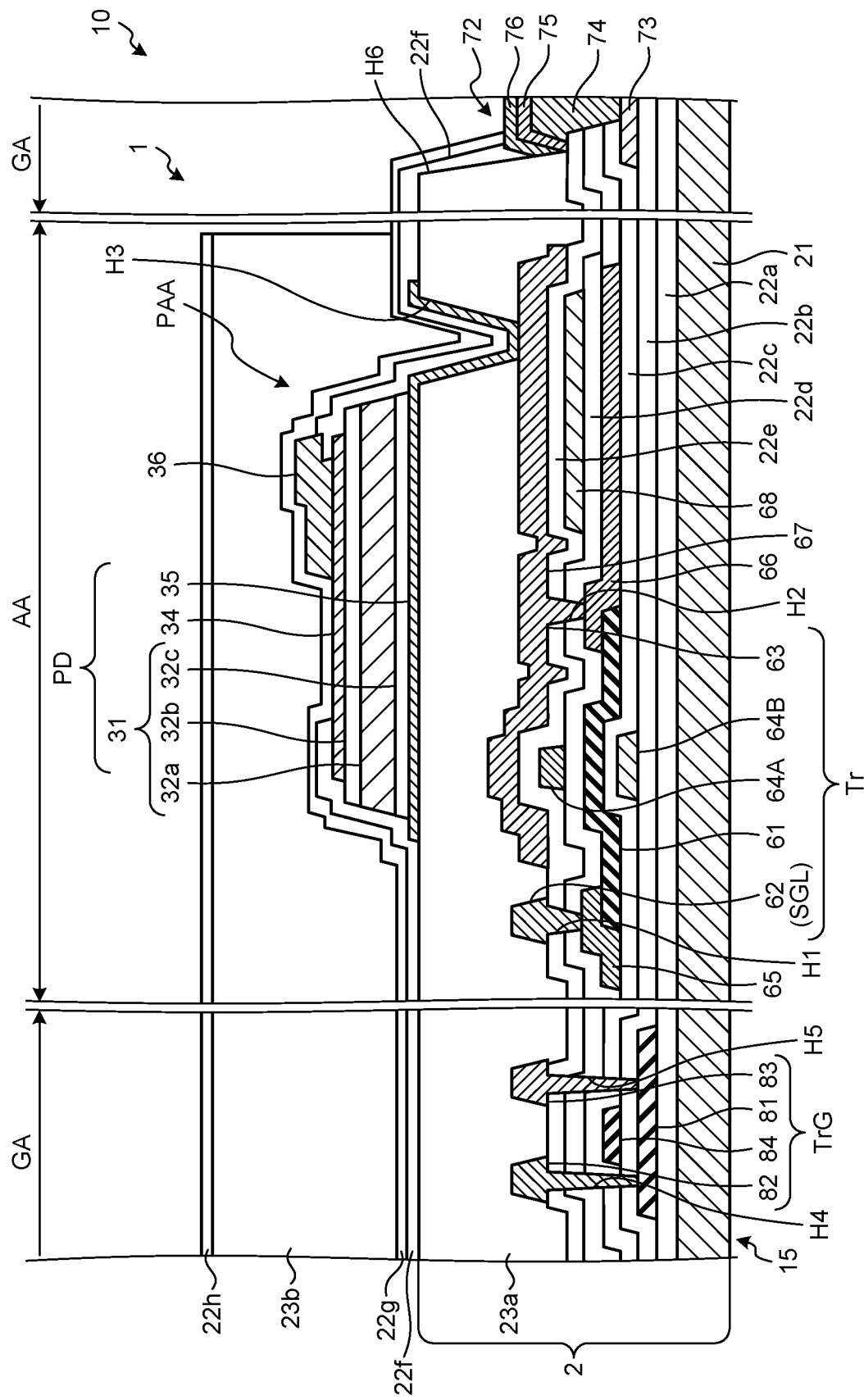
FIG. 8 is a sectional view taken along line A-A' of FIG. 7.

The following describes a detailed configuration of the detection device 1. FIG. 7 is a plan view schematically illustrating the partial detection area of the detection device according to the first embodiment. FIG. 8 is a sectional view taken along line A-A' of FIG. 7. To illustrate a relation between a layered structure of the detection area AA and a layered structure of the peripheral area GA, FIG. 8 illustrates the section taken along line A-A' and a section of a portion of the peripheral area GA including one of the second switching elements TrG in a schematically connected manner. FIG. 8 also illustrates a section of a portion of the peripheral area GA including a terminal portion 72 in a schematically connected manner.

In the description of the detection device 1, in a direction (third direction Dz) orthogonal to a surface of the insulating substrate 21, the term "upper side" refers to a direction from the insulating substrate 21 toward the light-receiving element PD, and the term "lower side" refers to a direction from the light-receiving element PD toward the insulating substrate 21. The term "plan view" refers to a case of viewing from the direction orthogonal to the surface of the insulating substrate 21.

As illustrated in FIG. 7, the partial detection area PAA is an area surrounded by the gate lines GCL and the signal lines SGL. In the present embodiment, each of the gate lines GCL includes a first gate line GCLA and a second gate line GCLB. The first gate line GCLA is provided so as to overlap the second gate line GCLB. The first gate line GCLA and the second gate line GCLB are provided in different layers with insulating layers (a third inorganic insulating layer 22c and a fourth inorganic insulating layer 22d (refer to FIG. 8)) interposed therebetween. The first gate line GCLA and the second gate line GCLB are electrically coupled to each other at any place and are supplied with the gate drive signals VGCL having the same potential. At least one of the first gate line GCLA and the second gate line GCLB is coupled to the gate line drive circuit 15. In FIG. 7, the first gate line GCLA has a different width from that of the second gate line GCLB. However, the first gate line GCLA may have the same width as that of the second gate line GCLB.

The light-receiving element PD is provided in the area surrounded by the gate lines GCL and the signal lines SGL. The light-receiving element PD includes a third semiconductor 31, an upper electrode 34, and a lower electrode 35. The light-receiving element PD is, for example, a photodiode of positive-intrinsic-negative (PIN) diode type or a photodiode made of an organic semiconductor.

Specifically, as illustrated in FIG. 8, the light-receiving element PD is configured such that the lower electrode 35, the third semiconductor 31, and the upper electrode 34 are stacked in the order of the lower electrode 35, the third semiconductor 31, and the upper electrode 34 on a first organic insulating layer 23a of a backplane 2. The backplane 2 is a drive circuit board that drives the sensor on a predetermined detection area basis. The backplane 2 includes the insulating substrate 21, the first switching element Tr, the second switching element TrG, and various types of wiring provided on the insulating substrate 21.

The third semiconductor 31 is of amorphous silicon (a-Si). The third semiconductor 31 includes an i-type semiconductor 32a, a p-type semiconductor 32b, and an n-type semiconductor 32c. The i-type semiconductor 32a, the p-type semiconductor 32b, and the n-type semiconductor 32c are specific examples of the photoelectric conversion elements. In FIG. 8, the n-type semiconductor 32c, the i-type semiconductor 32a, and the p-type semiconductor 32b are stacked in the order as listed, in the direction orthogonal to the surface of the insulating substrate 21. However, a reversed configuration may be employed. That is, the p-type semiconductor 32b, the i-type semiconductor 32a, and the n-type semiconductor 32c may be stacked in the order as listed. The third semiconductor 31 may be a photoelectric conversion element made of an organic semiconductor. In that case, the semiconductor 32a is formed of a bulk heterojunction of a p-type semiconductor and an n-type semiconductor, and the semiconductor 32b and the semiconductor 32c are each formed of a charge transport layer or a charge blocking layer of electrons and holes, respectively.

The lower electrode 35 is the anode of the light-receiving element PD and is an electrode for reading the detection signal Vdet. For example, a metal material such as molybdenum (Mo) or aluminum (Al) is used as the lower electrode 35. Alternatively, the lower electrode 35 may be a multilayered film having a plurality of stacked layers of these metal materials. The lower electrode 35 may be of a light-transmitting conductive material such as indium tin oxide (ITO).

The a-Si of the n-type semiconductor 32c is doped with impurities to form an n+ region. The a-Si of the p-type semiconductor 32b is doped with impurities to form a p+ region. The i-type semiconductor 32a is, for example, a non-doped intrinsic semiconductor and has lower conductivity than that of the n-type semiconductor 32c and the p-type semiconductor 32b.

The upper electrode 34 is the cathode of the light-receiving element PD and is an electrode for supplying the power supply signal SVS to the photoelectric conversion layer. The upper electrode 34 is a light-transmitting conductive layer of, for example, ITO. The upper electrode 34 is provided for each of the light-receiving element PD.

As illustrated in FIG. 8, a sixth inorganic insulating layer 22f and a seventh inorganic insulating layer 22g are provided on the upper side of the first organic insulating layer 23a. The sixth inorganic insulating layer 22f covers a peripheral portion of the upper electrode 34 and is provided with an opening at a position overlapping the upper electrode 34. Coupling wiring 36 is coupled to the upper electrode 34 at a portion of the upper electrode 34 not provided with the sixth inorganic insulating layer 22f. The seventh inorganic insulating layer 22g is provided on the upper side of the sixth inorganic insulating layer 22f so as to cover the upper electrode 34 and the coupling wiring 36. A second organic insulating layer 23b serving as a planarizing layer is provided on the upper side of the seventh inorganic insulating layer 22g. In the case of the photodiode of the organic semiconductor, an eighth inorganic insulating layer 22h may further be provided on the upper side of the second organic insulating layer 23b.

As illustrated in FIG. 7, the upper electrode 34 is coupled to a power supply signal line Lvs through the coupling wiring 36. The power supply signal line Lvs is wiring that supplies the power supply signal SVS to the light-receiving element PD. In the present embodiment, the power supply signal line Lvs extends in the second direction Dy so as to overlap the signal line SGL. The partial detection areas PAA arranged in the second direction Dy are coupled to the common power supply signal line Lvs. Such a configuration allows the partial detection area PAA to have a larger opening. The lower electrode 35, the third semiconductor 31, and the upper electrode 34 have a quadrilateral shape in the plan view. However, the shape of the lower electrode 35, the third semiconductor 31, and the upper electrode 34 is not limited thereto and can be changed as appropriate.

As illustrated in FIG. 7, the first switching element Tr is provided near an intersecting portion between the gate line GCL and the signal line SGL. The first switching element Tr includes a first semiconductor 61, a source electrode 62, a drain electrode 63, a first gate electrode 64A, and a second gate electrode 64B.

The first semiconductor 61 is an oxide semiconductor. The first semiconductor 61 is more preferably a transparent amorphous oxide semiconductor (TAOS) among types of the oxide semiconductor. Using the oxide semiconductor as the first switching element Tr can suppress a leakage current of the first switching element Tr. That is, the first switching element Tr can reduce the leakage current from the partial detection area PAA that is not selected during the reading period Pdet illustrated in FIG. 6. As a result, the detection device 1 can increase a signal-to-noise (S/N) ratio.

The first semiconductor 61 is provided along the first direction Dx and intersects the first gate electrode 64A and the second gate electrode 64B in the plan view. The first gate electrode 64A and the second gate electrode 64B are provided so as to branch from the first gate line GCLA and the second gate line GCLB, respectively. In other words, portions of the first gate line GCLA and the second gate line GCLB overlapping the first semiconductor 61 serve as the first gate electrode 64A and the second gate electrode 64B. Aluminum (Al), copper (Cu), silver (Ag), molybdenum (Mo), or an alloy of these materials is used as the first gate electrode 64A and the second gate electrode 64B. A channel area is formed at a portion of the first semiconductor 61 overlapping the first gate electrode 64A and the second gate electrode 64B.

One end of the first semiconductor 61 is coupled to the source electrode 62 through a contact hole H1. The other end of the first semiconductor 61 is coupled to the drain electrode 63 through a contact hole H2. A portion of the signal line SGL overlapping the first semiconductor 61 serves as the source electrode 62. A portion of the third conductive layer 67 overlapping the first semiconductor 61 serves as the drain electrode 63. The third conductive layer 67 is coupled to the lower electrode 35 through a contact hole H3. The above-described configuration allows the first switching element Tr to switch between coupling and decoupling between the light-receiving element PD and the signal line SGL.

The following describes a layer configuration of the first switching element Tr. As illustrated in FIG. 8, the first switching element Tr is provided above the insulating substrate 21. The insulating substrate 21 is, for example, a glass substrate. The insulating substrate 21 may alternatively be a resin substrate or a resin film formed of a resin such as polyimide. In the detection device 1, the first switching element Tr including the oxide semiconductor is formed above the insulating substrate 21. As a result, the detection device 1 can easily have an area of the detection area AA larger than that in a case of using a semiconductor substrate such as a silicon substrate.

The second gate electrode 64B is provided above the insulating substrate 21 with a first inorganic insulating layer 22a and a second inorganic insulating layer 22b interposed therebetween. For example, a silicon oxide (SiO) film, a silicon nitride (SiN) film, or a silicon oxynitride (SiON) film is used for the inorganic insulating layers such as the first inorganic insulating layers 22a and the second inorganic insulating layers 22b. Each of the inorganic insulating layers is not limited to a single layer, but may be a multi-layered film.

The third inorganic insulating layer 22c is provided on the upper side of the second inorganic insulating layer 22b so as to cover the second gate electrode 64B. The first semiconductor 61, a first conductive layer 65, and a second conductive layer 66 are provided on the upper side of the third inorganic insulating layer 22c. The first conductive layer 65 is provided so as to cover an end of the first semiconductor 61 coupled to the source electrode 62. The second conductive layer 66 is provided so as to cover an end of the first semiconductor 61 coupled to the drain electrode 63.

The fourth inorganic insulating layer 22d is provided above the third inorganic insulating layer 22c so as to cover the first semiconductor 61, the first conductive layer 65, and the second conductive layer 66. The first gate electrode 64A is provided above the fourth inorganic insulating layer 22d. The first semiconductor 61 is provided between the first gate electrode 64A and the second gate electrode 64B in a direction orthogonal to the insulating substrate 21. That is, the first switching element Tr has what is called a dual-gate structure. However, the first switching element Tr may have a top-gate structure in which the first gate electrode 64A is provided while the second gate electrode 64B is not provided, or a bottom-gate structure in which only the second gate electrode 64B is provided without the first gate electrode 64A being provided.

A fifth inorganic insulating layer 22e is provided above the fourth inorganic insulating layer 22d so as to cover the first gate electrode 64A. The source electrode 62 (signal line SGL) and the drain electrode 63 (third conductive layer 67) are provided above the fifth inorganic insulating layer 22e. In the present embodiment, the drain electrode 63 is the third conductive layer 67 provided above the first semiconductor 61 with the fourth inorganic insulating layer 22d and the fifth inorganic insulating layer 22e interposed therebetween. The fourth inorganic insulating layer 22d and the fifth inorganic insulating layer 22e are provided with the contact hole H1 and the contact hole H2. The first conductive layer 65 is exposed at the bottom of the contact hole H1. The source electrode 62 is electrically coupled to the first semiconductor 61 through the contact hole H1 and the first conductive layer 65. In the same manner, the second conductive layer 66 is exposed at the bottom of the contact hole H2. The drain electrode 63 is electrically coupled to the first semiconductor 61 through the contact hole H2 and the second conductive layer 66.

The first conductive layer 65 is provided at a portion overlapping at least the bottom of the contact hole H1 between the source electrode 62 and the first semiconductor 61, and contacts the first semiconductor 61. The second conductive layer 66 is provided at a portion overlapping at least the bottom of the contact hole H2 between the drain electrode 63 and the first semiconductor 61, and contacts the first semiconductor 61. Since the detection device 1 is provided with the first conductive layer 65 and the second conductive layer 66, the first semiconductor 61 can be restrained from being removed by an etching solution when the contact holes H1 and H2 are formed by etching. That is, in the detection device 1, the first switching elements Tr in the detection area AA and the second switching elements TrG in the peripheral area GA can be formed in the same process, so that the manufacturing cost can be reduced.

A metal material such as aluminum (Al), copper (Cu), silver (Ag), or molybdenum (Mo), or an alloy of these materials is used as the first conductive layer 65, the second conductive layer 66, and the third conductive layer 67. The first conductive layer 65 and the second conductive layer 66 only need to be made of a conductive material that restrains the etching from progressing when the contact holes H1 and H2 are formed.

The third conductive layer 67 is provided in an area overlapping the light-receiving element PD in the plan view. The third conductive layer 67 is also provided above the first semiconductor 61, the first gate electrode 64A, and the second gate electrode 64B. That is, the third conductive layer 67 is provided between the first gate electrode 64A and the lower electrode 35 in the direction orthogonal to the insulating substrate 21. This configuration causes the third conductive layer 67 to have a function as a protection layer for protecting the first switching element Tr.

The second conductive layer 66 extends so as to face the third conductive layer 67 in an area not overlapping the first semiconductor 61. A fourth conductive layer 68 is provided on the upper side of the fourth inorganic insulating layer 22d in an area not overlapping the first semiconductor 61. The fourth conductive layer 68 is provided between the second conductive layer 66 and the third conductive layer 67. This configuration forms a capacitance between the second conductive layer 66 and the fourth conductive layer 68, and a capacitance between the third conductive layer 67 and the fourth conductive layer 68. The capacitances formed by the second conductive layer 66, the third conductive layer 67, and the fourth conductive layer 68 serve as a capacitance of the capacitive element Ca illustrated in FIG. 5.

The first organic insulating layer 23a is provided on the upper side of the fifth inorganic insulating layer 22e so as to cover the source electrode 62 (signal line SGL) and the drain electrode 63 (third conductive layer 67). The first organic insulating layer 23a is a planarizing layer that planarizes asperities formed by the first switching elements Tr and various types of conductive layers. The light-receiving element PD is provided on the upper side of the first organic insulating layer 23a. The lower electrode 35 is electrically coupled to the third conductive layer 67 through the contact hole H3 provided in the first organic insulating layer 23a. That is, the third conductive layer 67 is electrically coupled to the lower electrode 35 serving as the anode of the light-receiving element PD and is provided between the light-receiving element PD and the first gate electrode 64A of the first switching element Tr.

The second switching elements TrG of the gate line drive circuit 15 are provided in the peripheral area GA. The second switching element TrG and the first switching element Tr are provided on the same insulating substrate 21. The second switching element TrG includes a second semiconductor 81, a source electrode 82, a drain electrode 83, and a gate electrode 84.

The second semiconductor 81 is of polysilicon. The second semiconductor 81 is more preferably of low-temperature polysilicon (hereinafter, referred to as low-temperature polycrystalline silicon (LTPS)). The second switching element TrG using LTPS can be produced at a process temperature of 600 degrees Celsius or lower. Therefore, circuits such as the gate line drive circuit 15 and the signal line selection circuit 16 as well as the first switching element Tr can be formed on the same substrate. Polysilicon has higher carrier mobility than that of a-Si. Therefore, the size of the gate line drive circuit 15 in the detection device 1 can be reduced by using polysilicon as the second switching elements TrG. As a result, the area of the peripheral area GA in the detection device 1 can be reduced. The second switching element TrG using polysilicon has higher reliability than that obtained using a-Si.

The second semiconductor 81 is provided on the upper side of the first inorganic insulating layer 22a. That is, the first semiconductor 61 of the first switching element Tr is provided in a position farther away from the insulating substrate 21 than the second semiconductor 81 of the second switching element TrG in the direction orthogonal to the insulating substrate 21. This configuration allows the second semiconductor 81 formed of polysilicon and the first semiconductor 61 formed of the oxide semiconductor to be formed on the same insulating substrate 21.

The gate electrode 84 is provided above the second semiconductor 81 with the second inorganic insulating layer 22b interposed therebetween. The gate electrode 84 is provided in the same layer as that of the second gate electrode 64B. The second switching element TrG has what is called the top-gate structure. However, the second switching element TrG may have the dual-gate structure or the bottom-gate structure.

The source electrode 82 and the drain electrode 83 are provided on the upper side of the fifth inorganic insulating layer 22e. The source electrode 82 and the drain electrode 83 are provided in the same layer as that of the source electrode 62 and the drain electrode 63 of the first switching element Tr. Contact holes H4 and H5 are provided through from the second inorganic insulating layer 22b to the fifth inorganic insulating layer 22e. The source electrode 82 is electrically coupled to the second semiconductor 81 through the contact hole H4. The drain electrode 83 is electrically coupled to the second semiconductor 81 through the contact hole H5.

The contact holes H4 and H5 are formed in four layers of the inorganic insulating layers (from the second inorganic insulating layer 22b to the fifth inorganic insulating layer 22e), and the contact holes H1 and H2 are formed in two layers of the inorganic insulating layers (the fourth inorganic insulating layer 22d and the fifth inorganic insulating layer 22e). That is, the length in the direction orthogonal to the insulating substrate 21 of the contact holes H4 and H5 is longer than that of the contact holes H1 and H2. Even in this case, the contact holes H1 and H2 and the contact holes H4 and H5 of the detection device 1 can be formed in the same process because the first switching element Tr is provided with the first conductive layer 65 and the second conductive layer 66.

The third switching element TrS included in the signal line selection circuit 16 illustrated in FIG. 4 may have the same configuration as that of the second switching element TrG. That is, the semiconductor of the third switching element TrS is of polysilicon and is more preferably of LTPS. In this case, the circuit scale of the signal line selection circuit 16 of the detection device 1 can be reduced. The semiconductor of the third switching element TrS is not limited to such materials and may be an oxide semiconductor, including a TAOS. In the same manner, the fourth switching element TrR included in the reset circuit 17 illustrated in FIG. 4 may also have the same configuration as that of the second switching element TrG. That is, the semiconductor of the fourth switching element TrR is of polysilicon and is more preferably of LTPS. In this case, the circuit scale of the reset circuit 17 of the detection device 1 can be reduced. The semiconductor of the fourth switching element TrR is not limited to such materials and may be an oxide semiconductor, including a TAOS.

The terminal portion 72 is provided at a position of the peripheral area GA different from an area thereof provided with the gate line drive circuit 15. The terminal portion 72 includes a first terminal conductive layer 73, a second terminal conductive layer 74, a third terminal conductive layer 75, and a fourth terminal conductive layer 76. The first terminal conductive layer 73 is provided in the same layer as that of the second gate electrode 64B above the second inorganic insulating layer 22b. A contact hole H6 is provided so as to extend through the third inorganic insulating layer 22c, the fourth inorganic insulating layer 22d, the fifth inorganic insulating layer 22e, and the first organic insulating layer 23a.

The second terminal conductive layer 74, the third terminal conductive layer 75, and the fourth terminal conductive layer 76 are stacked in the contact hole H6 in the order as listed and are electrically coupled to the first terminal conductive layer 73. The second terminal conductive layer 74 can be formed using the same material as and in the same process as those of the third conductive layer 67 and the like. The third terminal conductive layer 75 can be formed using the same material as and in the same process as those of the lower electrode 35. The fourth terminal conductive layer 76 can be formed using the same material as and in the same process as those of the coupling wiring 36 and the power supply signal line Lvs (refer to FIG. 7).

Although FIG. 8 illustrates the single terminal portion 72, a plurality of such terminal portions 72 are arranged with gaps interposed therebetween. The terminal portions 72 are electrically coupled to the flexible printed circuit board 71 (refer to FIG. 1) through, for example, an anisotropic conductive film (ACF).

The sensor 10 has the above-described configuration, and thereby, can appropriately detect the biological information on the user. However, the structure of the sensor 10 is not limited to the above-described structure as long as being capable of detecting the biological information on the user by receiving the light L using the light-receiving element PD. The sensor 10 may detect information other than the biological information as long as detecting the information by receiving the light L using the light-receiving element PD.

(Light Guide Body)

The following describes the light guide body 100. The light guide body 100 is a member for guiding the light L to the light-receiving elements PD. In the present embodiment, the light guide body 100 is formed of an organic material, more specifically, a polymer material, and is elastically deformable. The light guide body 100 is, however, not limited to an organic material as long as having a configuration described below.

Figure 9:
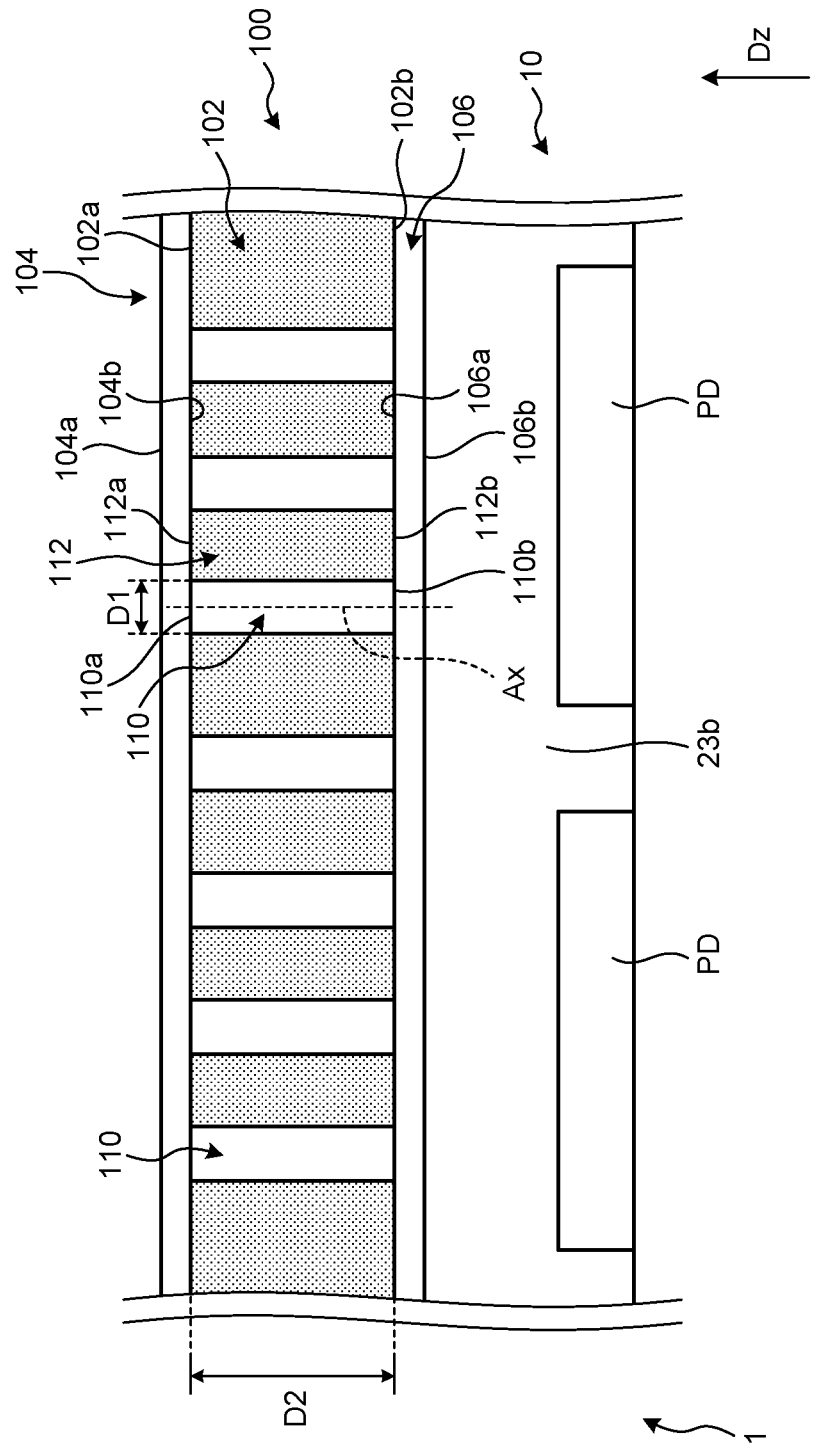
FIG. 9 is a schematic diagram of a light guide body according to the first embodiment.

FIGS. 9 and 10 are schematic diagrams of the light guide body according to the first embodiment. FIG. 9 is a sectional view of the light guide body 100, and FIG. 10 is a diagram obtained by viewing the light guide body 100 from the third direction Dz. As illustrated in FIG. 9, the light guide body 100 is provided on the upper side of the sensor 10 in the third direction Dz. That is, it can be said that the third direction Dz is a direction in which the light guide body 100 (light guide portion 102) and the sensor 10 (light-receiving elements PD) are stacked. The light guide body 100 includes the light guide portion 102 and light-transmitting layers 104 and 106. The light guide body 100 is a plate-like multilayered body stacked in the third direction Dz in the order of the light-transmitting layer 106, the light guide portion 102, and the light-transmitting layer 104. In the third direction Dz, the light-transmitting layer 106 is provided on the sensor 10 side, that is, on the light-receiving element PD side, and the light-transmitting layer 104 is provided on the detection target object (such as a finger Fg) side.

The light-transmitting layer 106 is a sheet-like member. A surface 106a on an upper side of the light-transmitting layer 106 contacts the light guide portion 102, and a surface 106b on the opposite side to the surface 106a (a lower side of the light-transmitting layer) contacts the sensor 10 (the second organic insulating layer 23b or the eighth inorganic insulating layer 22h in the example of FIG. 8). The light-transmitting layers 104 and 106 are each formed of a member that transmits the light L. Examples of the material of the light-transmitting layers 104 and 106 include polyethylene terephthalate (PET), polycarbonate (PC), polyethylene naphthalate (PEN), polyimide or transparent polyimide, cycloaliphatic epoxy, fluorene-based polyester, and polyphenylene sulfide (PPS). However, the material is not limited to these materials as long as being a member that transmits the light L. The light-transmitting layers 104 and 106 preferably have transmittance of the light L equal to that of a light guide path 110 of the light guide portion 102 to be described later. The refractive index of the light L of the light-transmitting layers 104 and 106 is preferably higher than the refractive index of the light L of the light guide path 110 of the light guide portion 102, and is preferably, for example, from 1.4 to 1.8. The transmittance and the refractive index may differ between the light-transmitting layer 104 and the light-transmitting layer 106.

The light-transmitting layers 104 and 106 are not essential components and may not be included in the light guide body 100. For example, the light guide body 100 may include neither the light-transmitting layer 104 nor the light-transmitting layer 106, or may include at least one of the light-transmitting layers 104 and 106.

The light guide portion 102 is a sheet-like member. A surface 102a on an upper side of the light guide portion 102 contacts a surface 104b of the light-transmitting layer 104, and a surface 102b on the opposite side to the surface 102a (a lower side of light guide portion) contacts the surface 106a of the light-transmitting layer 106. That is, the surface 102b of the light guide portion 102 faces the sensor 10 (light-receiving elements PD) with the light-transmitting layer 106 interposed therebetween. The light guide portion 102 includes the light guide paths 110 and a light-absorbing portion 112.

The light guide path 110 is a path capable of transmitting the light L. In the present embodiment, the light guide path 110 is a solid member capable of transmitting the light L. The light transmittance of the light guide path 110 is higher than the transmittance of the light L of the light-absorbing portion 112 to be described later. The light transmittance of the light guide path 110 is preferably from 50% to 100%. Herein, the transmittance of the light L refers to a ratio of an intensity of the output light L to an intensity of the incident light L. The light refractive index of the light guide path 110 is preferably from 1.40 to 1.70. The light guide path 110 is of an organic material, in more detail, of a polymer material and is, for example, of a silicone-based resin, an acrylic resin, or an epoxy-based resin. More specifically, the light guide path 110 is preferably of a photopolymerizable material that is cured by being irradiated with light and is preferably of, for example, a silicone-based photopolymerizable material, an acrylic photopolymerizable material, or an epoxy-based photopolymerizable material. The light guide path 110 may be of an organic material, such as the silicone-based photopolymerizable material, the acrylic photopolymerizable material, or the epoxy-based photopolymerizable material, including a material having a higher refractive index of the light L than that of the organic material. Examples of the material having a higher refractive index include transition metal alkoxides, such as titania and zirconia. However, the light guide path 110 is not limited to being formed of any of the above-mentioned materials as long as being a path capable of transmitting the light L. For example, the light guide path 110 may be a nonsolid state and may be a space including a gas such as air. In this case, the light guide path 110 can be called, in other words, an opening of the light guide portion 102, and the refractive index of the light L is one.

As illustrated in FIG. 10, a plurality of the light guide paths 110 are arranged in a matrix having a row-column configuration in the first direction Dx and the second direction Dy. In the example of FIG. 10, the light guide paths 110 are distributed in a square lattice pattern in the light guide portion 102 as viewed from the third direction Dz. However, the arrangement is not limited thereto and may be any arrangement. The light guide paths 110 may be distributed, for example, in a hexagonal lattice pattern. The pitch of the light guide paths 110, that is, the distance between centers of the adjacent light guide paths 110 is preferably equal for all the light guide paths 110. However, the pitch is not limited thereto and may vary on a per light guide path 110 basis.

As illustrated in FIG. 9, the light guide path 110 is provided throughout from the surface 102a to the surface 102b of the light guide portion 102. That is, it can be said that a surface 110a on an upper side of each light guide path 110 forms the surface 102a of the light guide portion 102, and it can be said that a surface 110b on the opposite side to the surface 110a (a lower side of the light guide path) forms the surface 102b of the light guide portion 102. A central axis Ax of the light guide path 110 extends substantially along the third direction Dz and is substantially orthogonal to the first direction Dx and the second direction Dy.

In the present embodiment, the light guide path 110 is cylindrical, and a diameter D1 thereof is constant in the third direction Dz. In the present embodiment, the diameters D1 of all the light guide paths 110 are equal. However, the light guide path 110 need not be cylindrical and may have a polygonal prism shape such as a quadratic prism shape. A length D2 denotes the length in the third direction Dz from the surface 110a to the surface 110b of the light guide path 110. The length D2 can also be said to be a length in the third direction Dz of the light guide portion 102. The length D2 is preferably from 10 μm to 300 μm. By setting the length D2 within such a numerical range, the light guide body 100 can be elastically deformed in a flexible manner to be applied to the detection device 1 having various shapes.

The ratio of the length D2 to the diameter D1 is defined as the aspect ratio of the light guide path 110. The aspect ratio of the light guide path 110 is preferably two or larger, more preferably five or larger, and still more preferably 10 or larger. Setting such an aspect ratio can reduce the angle of view when capturing an image of the detection target object (such as a finger Fg), and thus can reduce blurring of the detection target object at a distance when capturing the image thereof. The aspect ratio of the light guide path 110 is preferably, for example, 20 or smaller. Setting the aspect ratio to 20 or smaller allows the manufacturing to be appropriately performed.

As illustrated in FIG. 10, when viewed from the third direction Dz, the light guide paths 110 are provided so as to overlap the light-receiving elements PD. In more detail, when viewed from the third direction Dz, more than one of the light guide paths 110 overlap one light-receiving element PD. More specifically, each of the light-receiving elements PD overlaps more than one light guide path 110. That is, when viewed from the third direction Dz, more than one light guide path 110 is provided in an area in which one light-receiving element PD is formed. In the example of FIG. 10, nine of the light guide paths 110 overlap one light-receiving element PD. However, the number of the light guide paths 110 overlapping one light-receiving element PD is not limited to nine and may be any number that is a plural number. The light guide path 110 may be present between the adjacent light-receiving elements PD or may partially overlap the light-receiving element PD.

The light-absorbing portion 112 is provided so as to surround the periphery of the light guide paths 110. In the present embodiment, the light-absorbing portion 112 is provided over the entire area of the light guide portion 102 where the light guide paths 110 are not provided. Consequently, it can be said that the light guide paths 110 according to the present embodiment are formed at places of the light guide portion 102 surrounded by the light-absorbing portion 112. The light-absorbing portion 112 is provided throughout from the surface 102a to the surface 102b of the light guide portion 102. That is, it can be said that a surface 112a on an upper side of the light-absorbing portion 112 forms the surface 102a of the light guide portion 102, and it can be said that a surface 112b on the opposite side to the surface 112a (a lower side of the light-absorbing portion) forms the surface 102b of the light guide portion 102.

The light-absorbing portion 112 is formed of a member that absorbs the light L and has higher absorbance of the light L than the light guide path 110. The absorbance of the light L of the light-absorbing portion 112 is preferably from 70% to 100%, and more preferably 100%. Herein, the absorbance of the light L refers to a ratio of a difference between the intensity of the incident light L and the intensity of the output light L to the intensity of the incident light L. The light-absorbing portion 112 is of an organic material, in more detail, of a polymer material, and is, for example, of an acrylic resin, an epoxy resin, a polyimide resin, or a siloxane polymer-based resin. The light-absorbing portion 112 is also preferably a polymerizable material that is cured by being irradiated with light or by being heat-treated, and is preferably, for example, an acrylic photopolymerizable material having a small curing shrinkage ratio. Furthermore, the light-absorbing portion 112 may be any of the above-mentioned organic materials containing carbon black or titanium black such as titanium oxide or titanium oxynitride, a metal oxide such as an iron oxide, or further alternatively, a dye or an organic pigment that absorbs the light L.

Figure 11A:
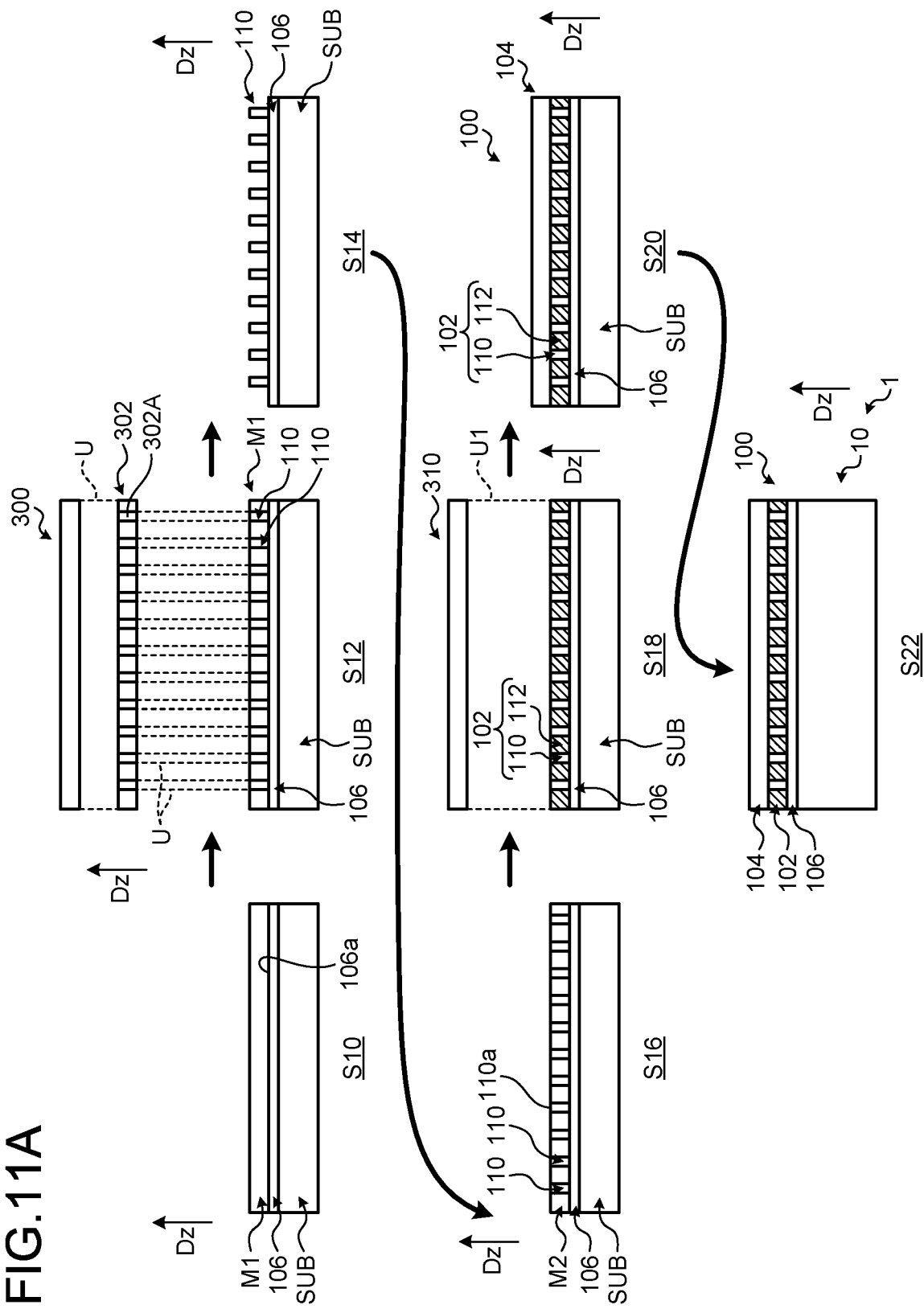
FIG. 11A is a schematic diagram explaining an exemplary method for manufacturing the light guide body according to the present embodiment.

The light guide body 100 has the above-described configuration. The following describes an exemplary method for manufacturing the light guide body 100. FIG. 11A is a schematic diagram explaining the exemplary method for manufacturing the light guide body according to the present embodiment. As illustrated in FIG. 11A, first, as illustrated in Step S10 (first application step), the light-transmitting layer 106 is formed on a substrate SUB, and a first organic material M1 is applied on the light-transmitting layer 106. The substrate SUB is a substrate used for forming the light guide body 100 and is, for example, a glass substrate. The first organic material M1 is formed, for example, in the entire area of the surface 106a of the light-transmitting layer 106. The first organic material M1 is an uncured member for the light guide paths 110. The first organic material M1 is, for example, a fluid organic material containing one or more types of photopolymerizable monomer components. The first organic material M1 may be a fluid organic material containing a plurality of components including one or more types of photopolymerizable monomer components and an oligomer that is difficult to be photopolymerized. The first organic material M1 may contain both a fluid organic material containing one or more types of photopolymerizable monomer components and a fluid organic material containing a plurality of components including one or more types of photopolymerizable monomer components and an oligomer that is difficult to be photopolymerized.

Then, as illustrated in Step S12 (light guide path forming step), patterned light U is emitted to the first organic material M1 provided on the light-transmitting layer 106. In the example illustrated in FIG. 11A, a light source 300 and a pattern forming portion 302 are used to emit the patterned light U. The light source 300 is a light source for generating the light U. The pattern forming portion 302 is a member provided with a plurality of transmission portions 302A. The transmission portions 302A are configured to transmit the light U. Each of the transmission portions 302A has an inside diameter corresponding to the diameter D1 (for example, an inside diameter equal to the diameter D1) of the light guide path 110. The transmission portions 302A are arranged with a pitch corresponding to the pitch of the light guide paths 110 (for example, at the same pitch as that of the light guide paths 110). The transmission portions 302A may be members that transmit the light U, or may be openings. The light U is light that can cure the first organic material M1 and is, for example, ultraviolet light.

At Step S12, the pattern forming portion 302 is disposed between the light source 300 and the first organic material M1, and the light U is emitted from the light source 300 toward a surface on an upper side of the first organic material M1. The light U from the light source 300 is emitted over the entire area of the pattern forming portion 302, for example. The light U emitted to the pattern forming portion 302 passes through the transmission portions 302A of the pattern forming portion 302 and is applied to the surface on the upper side of the first organic material M1. Consequently, the light U is emitted to only portions of the first organic material M1 corresponding to the pattern of the transmission portions 302A. The portions of the first organic material M1 irradiated with the light U are cured to be formed into the light guide paths 110. A portion not irradiated with the light U is not cured and remains to be the first organic material M1. That is, at Step S12, the light guide paths 110 perpendicularly extending along the third direction Dz are formed in the first organic material M1 that is not photopolymerized and thus not cured.

Figure 11B:
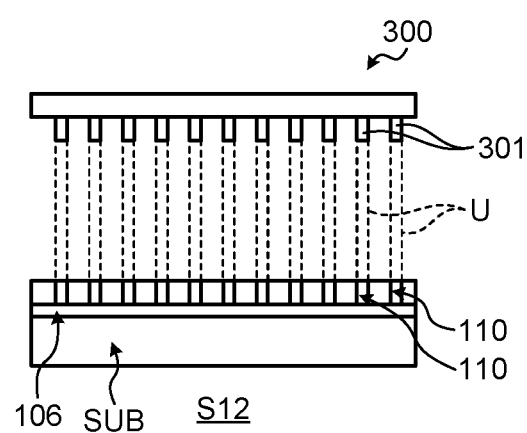
FIG. 11B is a schematic diagram explaining another exemplary method for manufacturing the light guide body according to the present embodiment.

At Step S12, the pattern forming portion 302 is used to apply the patterned light U to the first organic material M1. However, the present embodiment is not limited to using the pattern forming portion 302. FIG. 11B is a schematic diagram explaining another exemplary method for manufacturing the light guide body according to the present embodiment. For example, as illustrated in FIG. 11B, without providing the pattern forming portion, the light source 300 may be provided with a plurality of light sources 301 arranged in a pattern and may directly emit the light U (collimated light) that travels in a straight line from each of the light sources 301. When such collimated light is emitted and a self-organization effect of the material thereby forms a cylindrical microphase-separated pattern in the first organic material M1, the light guide paths 110 perpendicularly extending along the third direction Dz are formed in the first organic material M1 that is not photopolymerized and thus not cured.

Then, as illustrated in Step S14 (removal step), the first organic material M1 that is not photopolymerized and thus not cured is removed from the substrate SUB. The first organic material M1 is removed by, for example, immersing the first organic material M1 in a liquid that dissolves the first organic material M1. As a result, only the light guide paths 110 remain on the light-transmitting layer 106.

Then, as illustrated in Step S16 (second application step), a second organic material M2 is applied on the light-transmitting layer 106. The second organic material M2 is applied in an area on the light-transmitting layer 106 not provided with the light guide paths 110 (area from which the first organic material M1 has been removed). That is, the second organic material M2 is applied around each of the light guide paths 110. The second organic material M2 is the uncured light-absorbing portion 112 and has fluidity. At Step S16, the surface 110a on the upper side of the light guide path 110 is preferably not covered with the second organic material M2. However, even if the surface 110a is covered with the second organic material M2, the surface 110a may be exposed by later using a machining process or an etching process to remove an upper surface of the light-absorbing portion 112 formed from the second organic material M2.

Then, as illustrated in Step S18 (light-absorbing portion forming step), light U1 is emitted from a light source 310 to the second organic material M2 provided on the light-transmitting layer 106. The second organic material M2 is cured by the emission of the light U1 to be formed into the light-absorbing portion 112. As a result, the light guide portion 102 is formed on the light-transmitting layer 106. The light U1 may be, for example, ultraviolet light in the same manner as the light U. The second organic material M2 may be cured by heat to be formed into the light-absorbing portion 112. In this case, at Step S18, the second organic material M2 is cured by being heated, instead of being irradiated with the light U1. Alternatively, it may be cured by making combined use of the light and the heat. In that case, the light U1 is emitted to maintain the shape, and then, the heat is used for the curing.

Then, as illustrated in Step S20, the light-transmitting layer 104 is formed on the light guide portion 102. As a result, the light guide body 100 is formed on the substrate SUB. The light-transmitting layer 104 may be cured after being applied, or may be attached, in the form of a solid, onto the light guide portion 102.

Then, as illustrated in Step S22, the light guide body 100 is removed from the substrate SUB and is provided on the sensor 10. The detection device 1 is manufactured through further steps such as mounting of other members of the detection device 1. When removing the light guide body 100 from the substrate SUB, a laser lift-off method may be used to separate the light guide body 100 from the substrate SUB. In this case, a laser beam is emitted from a surface on the opposite side to a surface of the substrate SUB on which the light guide body 100 is provided. The laser beam passes through the substrate SUB and is emitted to a surface (surface 106b) of the light guide body 100 in contact with the substrate SUB. The laser beam separates the surface of the light guide body 100 in contact with the substrate SUB from the substrate SUB.

Figure 12:
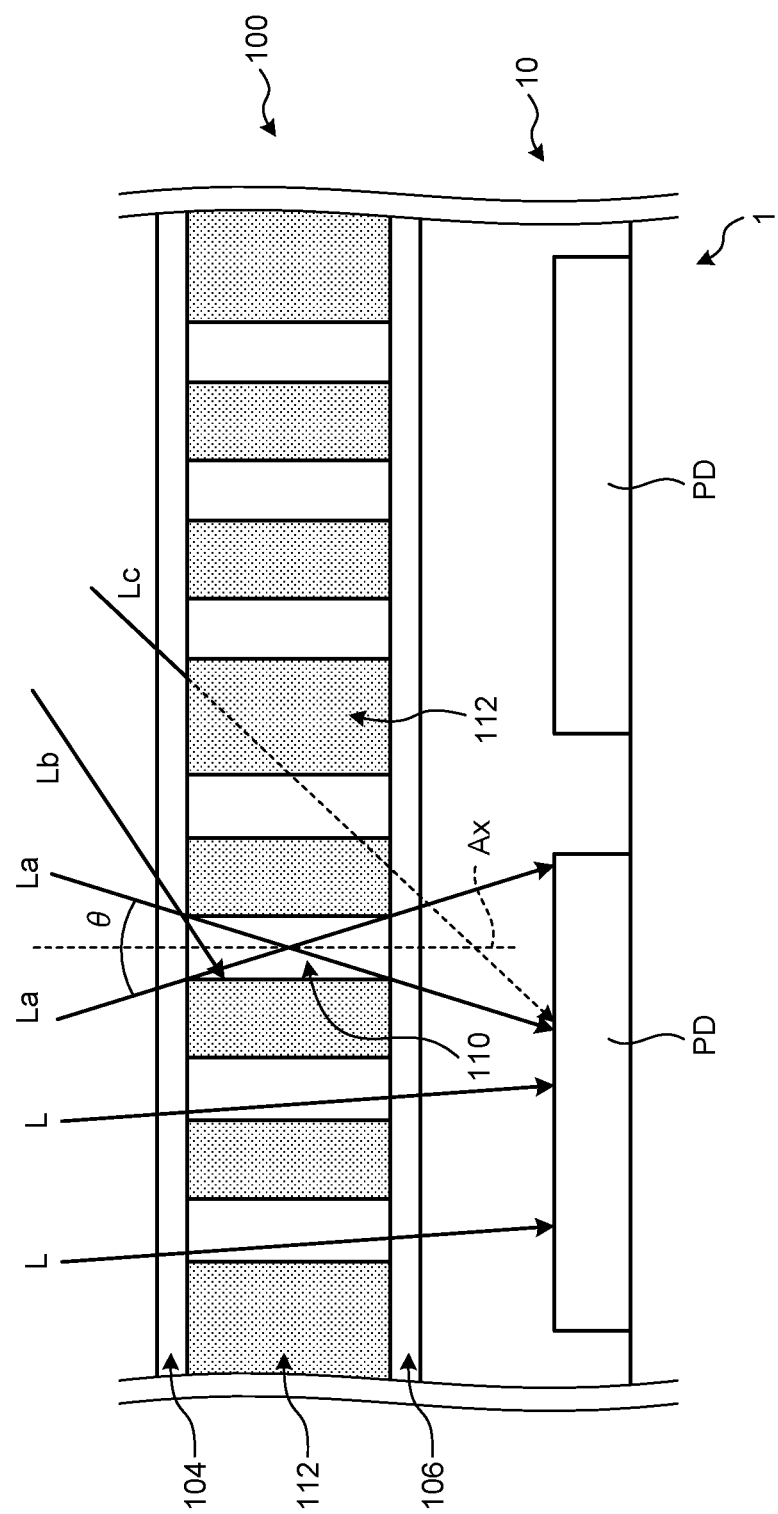
FIG. 12 is a schematic diagram explaining an example of the case of guiding light to a light-receiving element in a configuration of the first embodiment.

The following describes a case of guiding the light L to the light-receiving element PD. FIG. 12 is a schematic diagram explaining an example of the case of guiding the light to the light-receiving element in the configuration of the first embodiment. In the detection device that receives the light L to detect the information, the light L needs to be appropriately guided to the light-receiving element PD. For example, if the intensity of the light L guided to the light-receiving element PD is low, or if light from a place other than a place where the detection is to be performed is guided to the light-receiving element PD, the information may not be appropriately detected. If the light L coming from a wide area is guided to the light-receiving elements PD, the intensity of the light L received by each of the light-receiving elements PD is nearly evenly distributed, thus causing a phenomenon of, for example, blurring of an image. In contrast, as illustrated in FIG. 12, the detection device 1 according to the present embodiment includes the light guide portion 102 for guiding the light to the light-receiving elements PD. The light guide portion 102 is configured such that more than one of the light guide paths 110 overlap with one light-receiving element PD. Consequently, as illustrated in FIG. 12, the light L having passed through the light guide paths 110 can be guided to the light-receiving element PD. Therefore, the detection device 1 can restrain, for example, a reduction in the intensity of the light L guided to the light-receiving element PD. In addition, the light guide path 110 can limit an incident range angle θ serving as a range of the incident angle of the light L that can be incident on the light-receiving element PD through the light guide path 110. That is, an angle between the central axis Ax of the light guide path 110 and the traveling direction of the light La is within the range of the incident range angle θ, and thus the light La reaches the light-receiving element PD through the light guide path 110. In contrast, an angle between the central axis Ax of the light guide path 110 and the traveling direction of the light Lb is outside the range of the incident range angle θ, and thus the light Lb is applied to and absorbed by an inner perimeter surface of the light-absorbing portion 112 in the light guide path 110 and does not reach the light-receiving element PD. Therefore, with the detection device 1, the light L coming from a wide area is restrained from reaching the light-receiving element PD, and thus the depth of field can be increased. Even if light Lc from a place other than a place where the detection is to be performed by a certain light-receiving element PD (for example, light from a place where the detection is to be performed by another light-receiving element PD adjacent to the certain light-receiving element PD), comes toward the certain light-receiving element PD, the light Lc from the place other than the place where the detection is to be performed by the certain light-receiving element PD can be blocked from reaching the certain light-receiving element PD by the light-absorbing portion 112.

As described above, the detection device 1 according to the first embodiment includes the light-receiving elements PD that receive the light L, and the light guide portion 102 provided such that the surface 102b faces the light-receiving elements PD. The light guide portion 102 includes the light guide paths 110 and the light-absorbing portion 112. The light guide paths 110 are provided throughout from the surface 102a to the surface 102b of the light guide portion 102. The light-absorbing portion 112 has higher absorbance of the light L than that of the light guide path 110. In the detection device 1, when viewed from the direction (third direction Dz) in which the light-receiving elements PD and the light guide portion 102 are stacked, more than one of the light guide paths 110 overlap with one light-receiving element PD. By making the light guide paths 110 overlap with one light-receiving element PD, the detection device 1 according to the present embodiment can guide the light L through the light guide paths 110 to the light-receiving element PD, and thus can restrain the intensity of the light L guided to the light-receiving element PD from decreasing. By including the light-absorbing portion 112, the detection device 1 can restrain the light L from reaching the light-receiving element PD from a wide area and from areas other than the area where the detection is to be performed. As described above, the detection device 1 according to the present embodiment can appropriately guide the light L to the light-receiving element PD.

The light guide path 110 is formed of the solid member having higher transmittance of the light L than that of the light-absorbing portion 112. By forming the light guide path 110 made of the solid member having higher transmittance of the light L, the light L can be appropriately guided to the light-receiving element PD.

The light guide portion 102 is preferably formed of an organic material. By forming the light guide portion 102 made of an organic material, the light guide portion 102 can be elastically deformed in a flexible manner to be applied to the detection device 1 having various shapes.

A method for manufacturing the detection device 1 according to the present embodiment includes the first application step, the light guide path forming step, the removal step, the second application step, and the light-absorbing portion forming step. At the first application step, the first organic material M1 is applied onto the substrate SUB. At the light guide path forming step, the light U is emitted to an area of the first organic material M1 applied onto the substrate SUB where the light guide paths 110 are to be formed, the first organic material M1 in the area irradiated with the light U is cured, and the light guide paths 110 made of the cured first organic material M1 are formed. At the removal step, the uncured first organic material M1 is removed from the substrate SUB. At the second application step, the second organic material M2 is applied to an area on the substrate SUB where the light guide paths 110 are not formed. At the light-absorbing portion forming step, the light-absorbing portion 112 is formed by emitting the light U1 to the second organic material M2 on the substrate SUB, and curing the second organic material M2. With the manufacturing method according to the present embodiment, it is possible to appropriately manufacture the detection device 1 that appropriately guides the light L to the light-receiving elements PD.

(Modifications)

Figure 13:
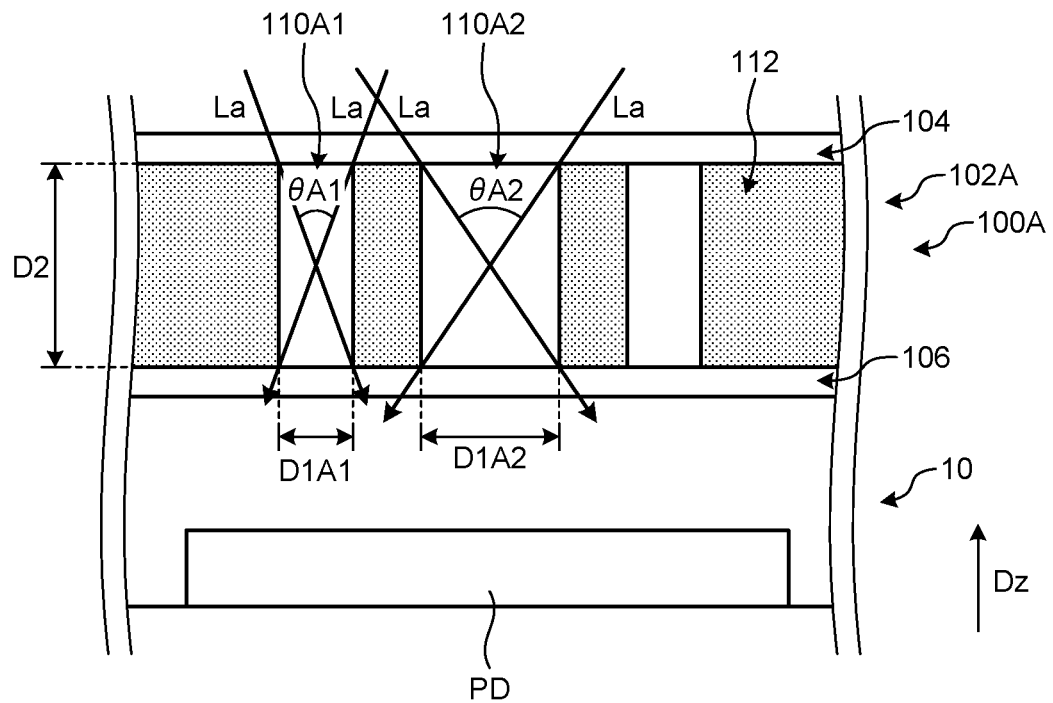
FIG. 13 is a schematic diagram of a light guide body according to a modification.

The following describes modifications of the first embodiment. In the first embodiment, all the light guide paths 110 have the same diameter. However, the diameter may vary from light guide path to light guide path, as illustrated in a modification below. FIG. 13 is a schematic diagram of a light guide body according to the modification. As illustrated in FIG. 13, light guide portions 102A of a light guide body 100A according to the modification include light guide paths 110A1 and 110A2 having different inside diameters. The light guide paths 110A1 and 110A2 overlap the same light-receiving element PD. A diameter D1A2 of the light guide path 110A2 is greater than a diameter D1A1 of the light guide path 110A1. Thus, the light guide paths 110A1 and 110A2 have different aspect ratios. The aspect ratio of the light guide path 110A2 (ratio of the length D2 to the diameter D1A2) is less than the aspect ratio of the light guide path 110A1 (ratio of the length D2 to the diameter D1A1). For example, the aspect ratio of the light guide path 110A2 is preferably equal to or greater than 2, and the aspect ratio of the light guide path 110A1 is preferably equal to or greater than 10. It is possible, by making the aspect ratios different from each other in this manner, to cause an incident range angle θA1 serving as a range of the incident angle of the light L that can be incident on the light-receiving element PD through the light guide path 110A1 to be smaller than an incident range angle θA2 serving as a range of the incident angle of the light L that can be incident on the light-receiving element PD through the light guide path 110A2. As a result, the depth of field in the light guide path 110A1 can be increased.

As described above, in the case of the light guide paths 110A, the light guide paths overlapping one light-receiving element PD have different aspect ratios from each other. By making the aspect ratios different from each other in this manner, the different types of biological information can be appropriately detected. For example, the fingerprint can be detected as the biological information by emitting the visible light as the light L0 and guiding the light L of the visible light as the reflected light thereof to the light-receiving elements PD. In addition, for example, the vascular pattern can be detected as the biological information by emitting the near-infrared light as the light L0 and guiding the light L of the near-infrared light as the reflected light thereof to the light-receiving elements PD. In this case, the fingerprint can be accurately detected by causing the light L of the visible light to reach the light-receiving elements PD through the light guide paths 110A1. In addition, the vascular pattern can be accurately detected by causing the light L of the near-infrared light to reach the light-receiving elements PD through the light guide paths 110A2. For example, each of the light guide paths can be appropriately used by providing a filter that transmits the visible light and absorbs the near-infrared light in the light guide path 110A1 and by providing a filter that transmits the near-infrared light and absorbs the visible light in the light guide path 110A2. However, a configuration with such filters is not essential. While FIG. 13 illustrates the configuration in which the two light guide paths: the light guide path 110A1 and the light guide path 110A2, have different diameters and different aspect ratios, three or more light guide paths may have different diameters and different aspect ratios from one another.

Figure 14:
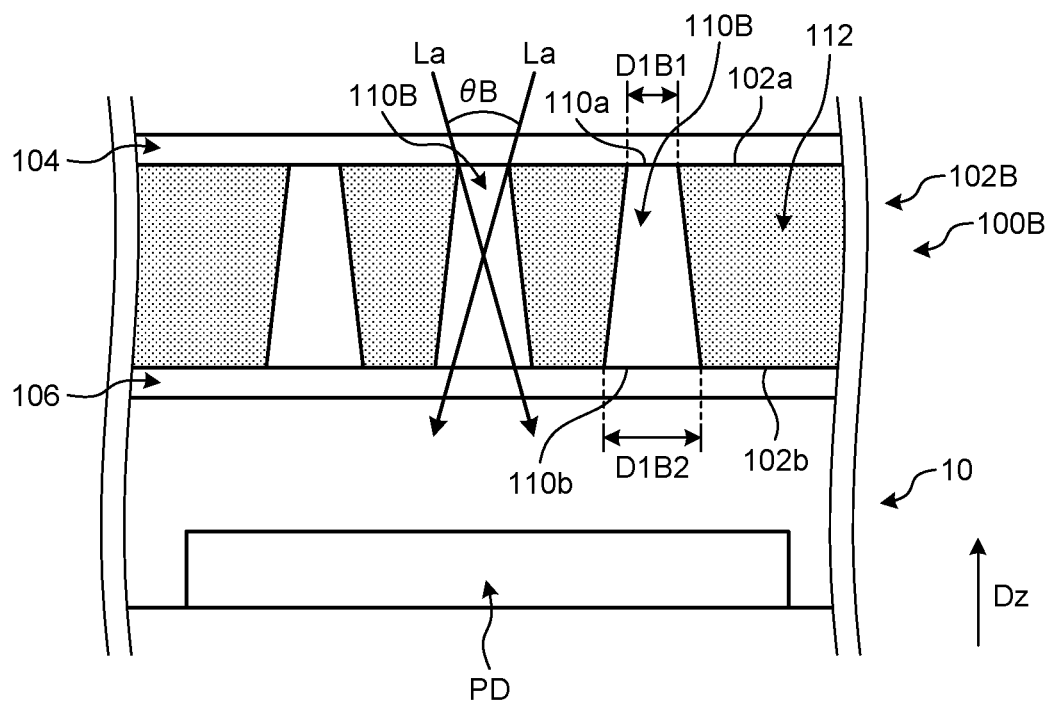
FIG. 14 is a schematic diagram of a light guide body according to another modification.
Figure 15:
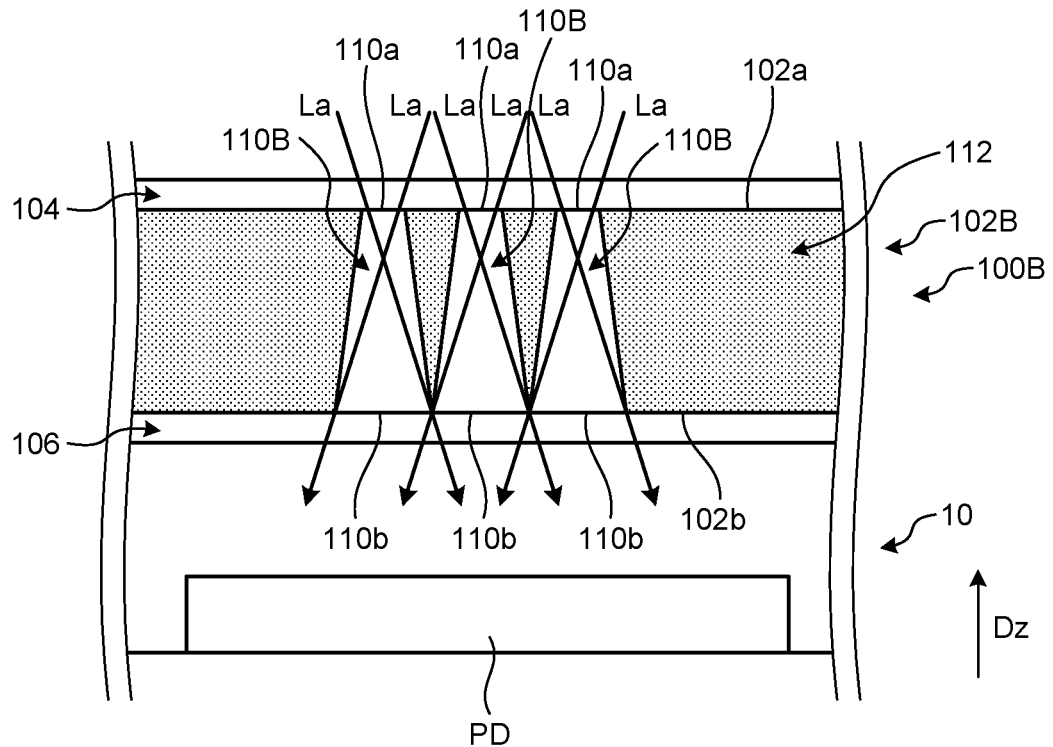
FIG. 15 is a schematic diagram of the light guide body according to another modification.

The following describes the other modifications of the first embodiment. In the first embodiment, the diameter D1 of the light guide path 110 is constant at each position in the third direction Dz. However, the diameter D1 of the light guide path 110 may vary with the position in the third direction Dz. FIGS. 14 and 15 are schematic diagrams of a light guide body according to another modification. As illustrated in FIG. 14, in a light guide portion 102B of a light guide body 100B according to another modification, the diameter of a light guide path 110B varies with the position in the third direction Dz. More specifically, the light guide path 110B has a forward tapered shape with a diameter decreasing from the surface 110b (surface 102b) toward the surface 110a (surface 102a). That is, a diameter D1B1 on the surface 110a side of the light guide path 110B is less than a diameter D1B2 on the surface 110b side of the light guide path 110B.

As described above, since the diameter of the light guide path 110B decreases toward the surface 102a, an incident range angle θB serving as a range of the incident angle of the light L that can incident on the light-receiving element PD through the light guide path 110B can be smaller than, for example, that in a case where the diameter is constant. That is, the thickness of the light guide portion 102B can be effectively reduced by employing the forward tapered shape when achieving the same aspect ratio as that in the case where the diameter D1 of the light guide path 110 is constant. Thus, the light L coming from a wide area can be restrained from reaching the light-receiving element PD, and the depth of field can be increased to appropriately guide the light L to the light-receiving element PD.

As illustrated in FIG. 15, portions of the surface 110b of the adjacent light guide paths 110B may contact each other. In other words, the light-absorbing portion 112 may not be provided between the outer perimeter portion of the surface 110b of one of the light guide paths 110B and the outer perimeter portion of the surface 110b of another of the light guide paths 110B adjacent to the one of the light guide path 110B. By contacting the surfaces 110b of the adjacent light guide paths 110B with each other in this manner, the light beams La having passed through the respective light guide paths 110B can reach the light-receiving element PD in a state overlapping each other, and whereby the intensity of the light can be increased.

The two modifications described above may be combined such that the diameter of each of the light guide path 110 varies with its position in the third direction Dz while the light guide paths 110 have different aspect ratios. The two modifications can be applied to a second embodiment and a third embodiment described below.

Second Embodiment

The following describes the second embodiment. While the light guide portion 102 of the first embodiment includes the light guide paths 110 and the light-absorbing portion 112, the light guide portion of the second embodiment further includes low-refractive-index portions. In the second embodiment, portions having configurations common to those of the first embodiment will not be described.

Figure 16:
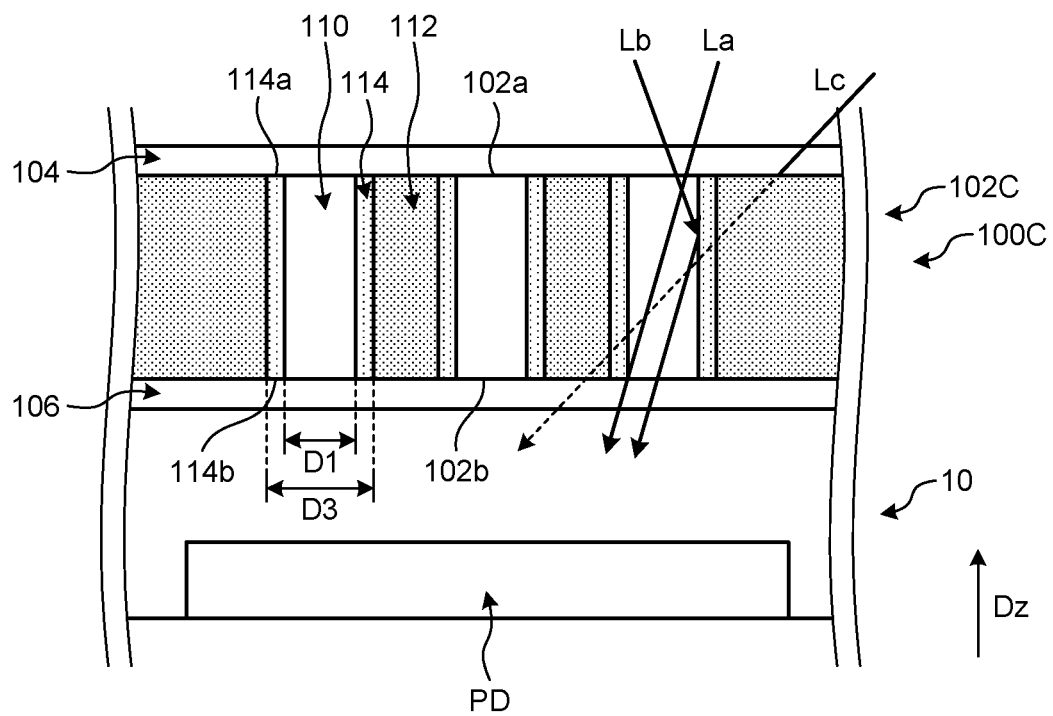
FIG. 16 is a schematic diagram of a light guide body according to a second embodiment.
Figure 17:
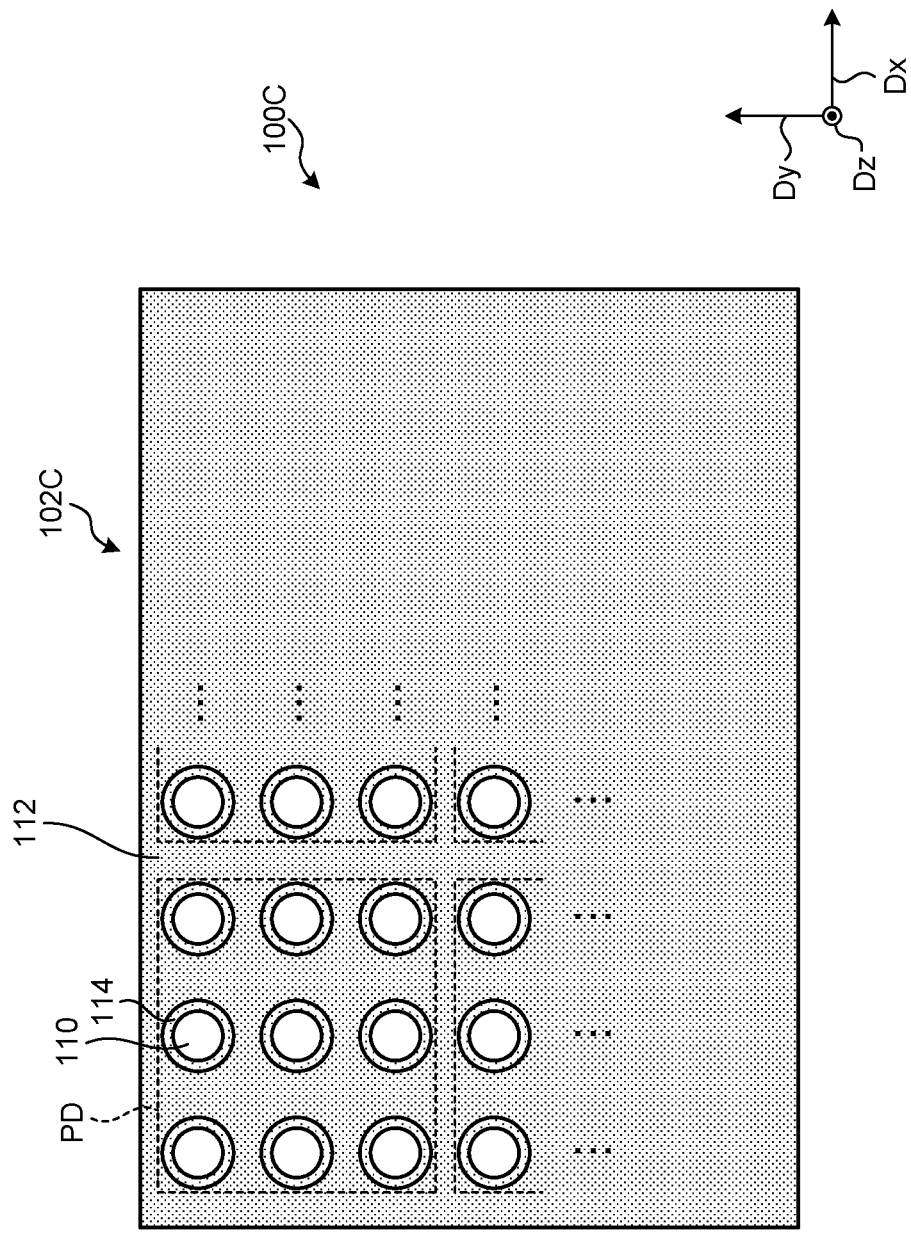
FIG. 17 is another schematic diagram of the light guide body according to the second embodiment.

FIGS. 16 and 17 are schematic diagrams of a light guide body according to the second embodiment. As illustrated in FIG. 16, a light guide portion 102C of a light guide body 100C according to the second embodiment includes the light guide paths 110, the light-absorbing portion 112, and low-refractive-index portions 114. Each of the low-refractive-index portions 114 is a member having a lower refractive index of the light L than that of the light guide path 110. The refractive index of the light L of the low-refractive-index portion 114 is preferably from 1.3 to 1.6. The transmittance of the light L of the low-refractive-index portion 114 is preferably higher than that of the light-absorbing portion 112. The light transmittance of the low-refractive-index portion 114 is preferably from 50% to 100%.

As illustrated in FIG. 17, the low-refractive-index portion 114 is provided for each of the light guide paths 110, and each of the low-refractive-index portions 114 is provided so as to surround the periphery of the corresponding light guide path 110. That is, the low-refractive-index portions 114 are provided so as to correspond to the light guide paths 110. As illustrated in FIG. 16, the low-refractive-index portion 114 is provided throughout from the surface 102a to the surface 102b of the light guide portion 102. That is, it can be said that a surface 114a on an upper side of each low-refractive-index portion 114 forms the surface 102a of the light guide portion 102, and it can be said that a surface 114b on the opposite side to the surface 114a (a lower side of the low-refractive-index portion) forms the surface 102b of the light guide portion 102. When a diameter D3 denotes the outside diameter of the low-refractive-index portion 114, the diameter D3 is preferably 1.0 to 1.2 times the diameter D1 of the light guide path 110. In the second embodiment, the light-absorbing portion 112 is provided so as to surround the periphery of the low-refractive-index portions 114. That is, the light-absorbing portion 112 is provided over the entire area of the light guide portion 102 where neither the low-refractive-index portions 114 nor the light guide paths 110 are provided. Thus, it can be said that the light guide paths 110 according to the second embodiment are formed in places of the light guide portion 102 surrounded by the low-refractive-index portions 114.

The low-refractive-index portion 114 may be of any material and may be, for example, of the same material as that of the light guide path 110. In this case, for example, the first organic material M1 described using FIG. 11A is a material that contains a low-molecular-weight acrylic monomer having a n-electron conjugated system and an oligomer that contains a siloxane bond having a low refractive index and is difficult to be photopolymerized. The oligomer component has a greater molecular weight than that of the monomer. When such a first organic material M1 is used to perform the processing at Step S12 of FIG. 11A, the acrylic monomer increases in a central portion of an area irradiated with the light L. As a result, the central portion has a higher refractive index, and the outside in the radial direction of the central portion has a lower refractive index. That is, the central portion becomes the light guide path 110, and the outside portion in the radial direction thereof becomes the low-refractive-index portion 114. Thus, the light guide paths 110 and the low-refractive-index portions 114 can be formed. However, this manufacturing method and the material are merely examples.

As described above, the light guide portion 102C further includes the low-refractive-index portion 114 having a lower refractive index of the light L than that of the light guide path 110. The low-refractive-index portion 114 surrounds the periphery of each of the light guide paths 110, and the light-absorbing portion 112 surrounds the periphery of each of the low-refractive-index portions 144. In the second embodiment, as illustrated in FIG. 16, the light Lb entered in the light guide path 110 and emitted to an outer perimeter surface of the light guide path 110 travels while being reflected by an interface with the low-refractive-index portion 114, and reaches the light-receiving element PD. In the case of the first embodiment, the low-refractive-index portion 114 is not provided, and whereby the light Lb entered the light guide path 110 and emitted to the outer perimeter surface of the light guide path 110 is absorbed by the light-absorbing portion 112 and does not reach the light-receiving element PD. Thus, in the first embodiment, the light L coming from a wide area can be restrained from reaching the light-receiving element PD. However, a case is possible where the intensity of the light is insufficient because the light Lb does not reach the light-receiving element PD. In such a case, when the low-refractive-index portion 114 is provided as in the second embodiment, the light Lb can reach the light-receiving element PD while restraining the light L (for example, the light Lc) from reaching from a wide area, and the insufficiency of intensity of the light can also be appropriately prevented. Therefore, according to the second embodiment, the light L can be appropriately guided to the light-receiving element PD.

(Modifications)

Figure 18:
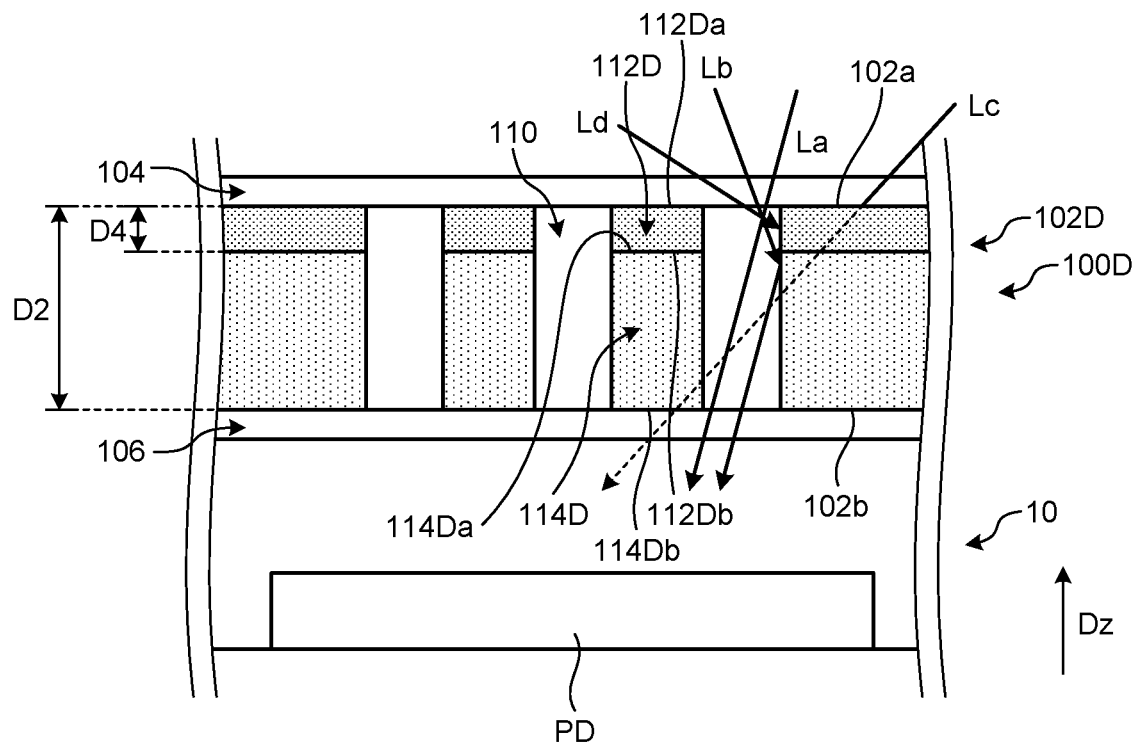
FIG. 18 is a schematic diagram of a light guide body according to a modification.

The following describes modifications of the second embodiment. FIG. 18 is a schematic diagram of a light guide body according to a modification. The second embodiment has the configuration in which the low-refractive-index portions 114 surround the periphery of the light guide paths 110, and the light-absorbing portion 112 surrounds the periphery of the low-refractive-index portions 114. However, the structure of the light guide paths 110, the low-refractive-index portions 114, and the light-absorbing portion 112 is not limited to such a configuration. For example, as illustrated in a light guide portion 102D of a light guide body 100D according to the modification of FIG. 18, the light guide portion may have a configuration including the light guide paths 110, a low-refractive-index portion 114D, and a light-absorbing portion 112D. The low-refractive-index portion 114D surrounds the periphery of the light guide paths 110, but does not surround the entire area in the third direction Dz of the light guide paths 110, and surrounds only a partial area in the third direction Dz of the light guide paths 110. Specifically, a surface 114db on a lower side of the low-refractive-index portion 114D is located at the same position as the surface 102b of the light guide portion 102D, but a surface 114Da on an upper side of the low-refractive-index portion 114D is located on the surface 102b side, that is, the lower side than the surface 102a of the light guide portion 102D. The low-refractive-index portion 114D covers the periphery of the light guide paths 110 in an area from the surface 114Da to the surface 114db.

The light-absorbing portion 112D is provided on the surface 114Da of the low-refractive-index portion 114D and surrounds the periphery of the light guide paths 110. A surface 112db on the lower side of the light-absorbing portion 112D contacts the surface 114Da of the low-refractive-index portion 114D, and a surface 112Da on the upper side of the light-absorbing portion 112D is located in the same position as the surface 102a of the light guide portion 102. The light-absorbing portion 112D covers the periphery of the light guide paths 110 in an area from the surface 112Da to the surface 112db. A length D4 in the third direction Dz of the light-absorbing portion 112D is preferably 0.3 to 1.0 times the length D2 in the third direction Dz of the light guide path 110.

As described above, in the light guide portion 102D, the low-refractive-index portion 114D surrounds the periphery of each of the light guide paths 110, and the light-absorbing portion 112D is provided on the surface 114Da side of the low-refractive-index portion 114D. With such a configuration, the light Lc coming from a wide area can be absorbed by the upper side light-absorbing portion 112D so as to be restrained from reaching the light-receiving element PD. While the light Lb entered the light guide path 110 and emitted to the outer perimeter surface of the light guide path 110 is caused to be reflected by the inner perimeter surface of the low-refractive-index portion 114D and to reach the light-receiving element PD, light Ld having a smaller incident angle (having a smaller incident angle with respect to the surface 102a) than that of the light Lb can be absorbed by the inner perimeter surface of the upper light-absorbing portion 112D so as to restrain the light L from reaching from a wide area.

Figure 19:
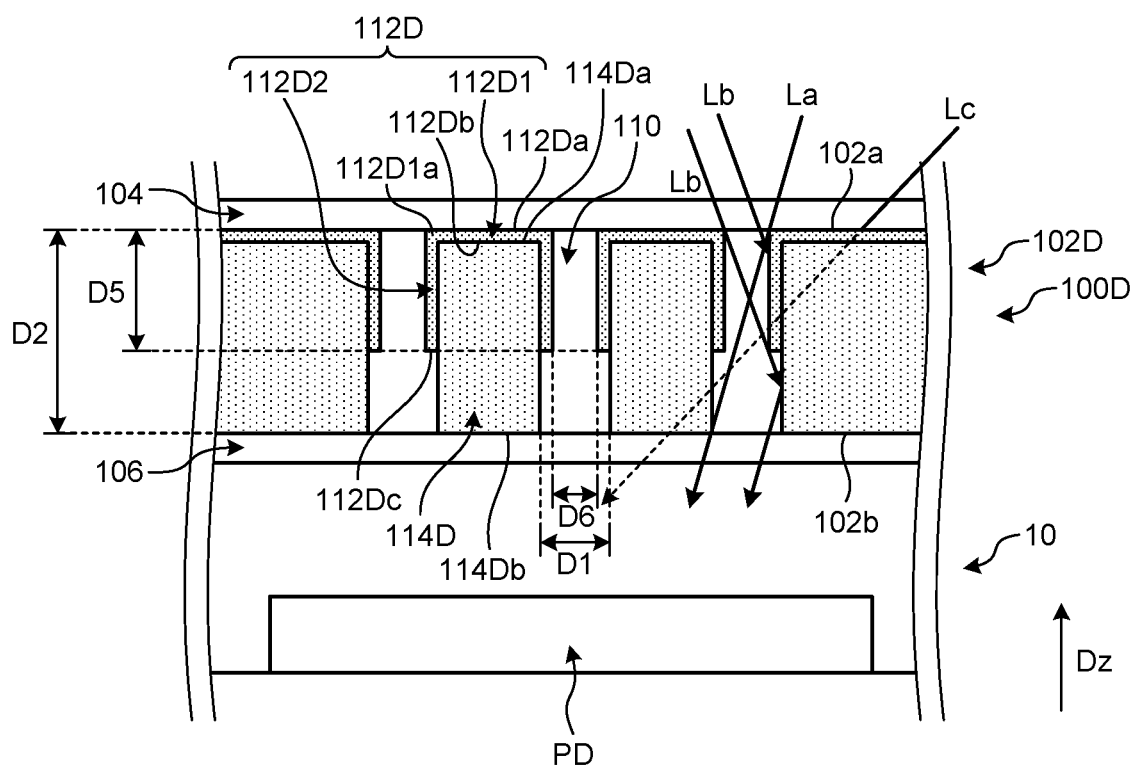
FIG. 19 is a schematic diagram of the light guide body according to another modification.

The following describes another modification of the second embodiment. FIG. 19 is a schematic diagram of the light guide body according to the modification. For example, as illustrated in FIG. 19, the light-absorbing portion 112D of the light guide body 100D may include a first light-absorbing portion 112D1 and a second light-absorbing portion 112D2. The first light-absorbing portion 112D1 is a portion of the light-absorbing portion 112D provided on the surface 114Da of the low-refractive-index portion 114D. The second light-absorbing portion 112D2 extends from an end 112D1a of the first light-absorbing portion 112D1, which is in contact with the light guide portion 102D, to an end 112Dc, that is, extends toward the surface 102b or the light-receiving element PD. The second light-absorbing portion 112D2 surrounds the periphery of the light guide path 110 from the end 112D1a to the end 112Dc. The second light-absorbing portion 112D2 is surrounded by the low-refractive-index portion 114D from the end 112D1a to the end 112Dc. From the end 112Dc to the surface 102b, the second light-absorbing portion 112D2 is not provided, and therefore, the low-refractive-index portion 114D surrounds the periphery of the light guide path 110.

A length D5 in the third direction Dz of the second light-absorbing portion 112D2 is preferably 0.2 to 1.0 times the length D2 of the light guide path 110. An inside diameter D6 of the second light-absorbing portion 112D2 is preferably 0.7 to 1.0 times the diameter D1 of the light guide path 110.

As described above, in the example of FIG. 19, the light-absorbing portion 112D includes the first light-absorbing portion 112D1 that is provided on the surface 114Da side of the low-refractive-index portion 114D and the second light-absorbing portion 112D2 that extends from the end 112D1a on the light guide portion 102D side of the first light-absorbing portion 112D1 toward the surface 102b and surrounds the periphery of the light guide path 110. When such a structure is employed, the light Lb that has entered the light guide path 110 can be caused to be reflected by the low-refractive-index portion 114D below the second light-absorbing portion 112D2 and to reach the light-receiving element PD. In addition, the light Ld having a smaller incident angle (having a smaller incident angle with respect to the surface 102a) than that of the light Lb can be absorbed by the inner perimeter surface of the second light-absorbing portion 112D2 so as to be restrained from reaching the light-receiving element PD.

Third Embodiment

The following describes the third embodiment. The third embodiment differs from the first embodiment in that the light guide portion includes selective light-absorbing portions 118. In the third embodiment, portions having configurations common to those of the first embodiment will not be described.

Figure 20:
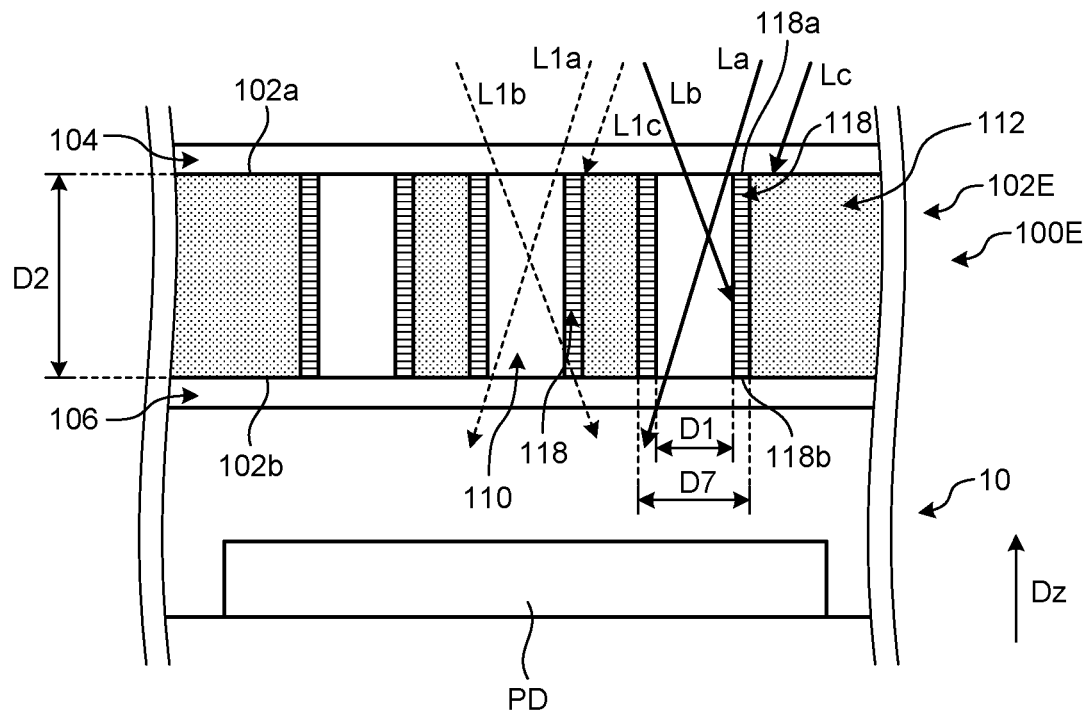
FIG. 20 is a schematic diagram of a light guide body according to a third embodiment.

FIG. 20 is a schematic diagram of a light guide body according to the third embodiment. As illustrated in FIG. 20, a light guide portion 102E of a light guide body 100E according to the third embodiment includes the light guide paths 110, the light-absorbing portion 112, and the selective light-absorbing portions 118. In the third embodiment, the light guide paths 110 transmit both the light L of the visible light and the light L of the near-infrared light. The light-absorbing portion 112 absorbs both the light L of the visible light and the light L of the near-infrared light. The selective light-absorbing portions 118 absorb the light L of the visible light, but transmit the light L of the near-infrared light. Each of the selective light-absorbing portions 118 has higher absorbance of the light L of the visible light than the light guide path 110 and has higher transmittance of the light L of the near-infrared light than the light-absorbing portion 112. The absorbance of the light L of the visible light of the selective light-absorbing portions 118 is preferably from 70% to 100%, and more preferably 100%. The transmittance of the light L of the near-infrared light of the selective light-absorbing portions 118 is preferably from 70% to 100%, and more preferably 100%.

In the same manner as the low-refractive-index portion 114 of the second embodiment, the selective light-absorbing portion 118 is provided for each of the light guide paths 110, and each of the selective light-absorbing portions 118 is provided so as to surround the periphery of the light guide path 110. That is, the selective light-absorbing portions 118 are provided so as to correspond to the light guide paths 110. The selective light-absorbing portion 118 is provided throughout from the surface 102a to the surface 102b of the light guide portion 102. That is, it can be said that a surface 118a on an upper side of each selective light-absorbing portion 118 forms the surface 102a of the light guide portion 102, and it can be said that a surface 118b on the opposite side to the surface 118a (a lower side of the selective light-absorbing portion) forms the surface 102b of the light guide portion 102. When a diameter D7 denotes the outside diameter of the selective light-absorbing portion 118, a ratio of the length D2 to the diameter D7 as the aspect ratio of the selective light-absorbing portion 118 is smaller than a ratio of the length D2 to the diameter D1 as the aspect ratio of the light guide path 110. The aspect ratio of the selective light-absorbing portion 118 is preferably 0.2 to 1.0 times the aspect ratio of the light guide path 110. With such an aspect ratio, the vascular pattern and the fingerprint can be appropriately detected by appropriately receiving the near-infrared light and the visible light. The aspect ratio of the selective light-absorbing portion 118 is preferably 2 or larger, and preferably 20 or smaller.

The selective light-absorbing portions 118 are formed of an organic material, more specifically, a polymer material, such as a polymer material containing a pigment or a dye that absorbs visible light.

In the third embodiment, the light-absorbing portion 112 is provided so as to surround the periphery of the selective light-absorbing portions 118. That is, the light-absorbing portion 112 is provided over the entire area of the light guide portion 102 where neither the selective light-absorbing portions 118 nor the light guide paths 110 are provided. Thus, it can be said that the light guide paths 110 according to the third embodiment is formed in places of the light guide portion 102 surrounded by the selective light-absorbing portions 118.

As described above, the light guide portion 102E further includes the selective light-absorbing portions 118. The selective light-absorbing portion 118 has higher absorbance of the light L of the visible light than the light guide path 110 and has higher transmittance of the light L of the near-infrared light than the light-absorbing portion 112. The selective light-absorbing portion 118 surrounds the periphery of each of the light guide paths 110, and the light-absorbing portion 112 surrounds the periphery of each of the selective light-absorbing portions 118. In the third embodiment, as illustrated in FIG. 20, the light Lc of the visible light and light L1c of the near-infrared light coming from a place other than a place where the detection is to be performed, are absorbed by the light-absorbing portion 112 and thus can be restrained from reaching the light-receiving element PD. The light La of the visible light and light L1a of the near-infrared light entered the light guide path 110 but not incident on the inner perimeter surface of the selective light-absorbing portion 118 travel through the light guide path 110 to reach the light-receiving element PD. The light Lb of the visible light having a smaller incident angle (having a smaller incident angle with respect to the surface 102a) than that of the light La of the visible light is incident on the inner perimeter surface of the selective light-absorbing portion 118 in the light guide path 110 and is absorbed by the selective light-absorbing portion 118 so as to be restrained from reaching the light-receiving element PD. In contrast, light L1b of the near-infrared light having a smaller incident angle than that of the light L1a of the near-infrared light is incident on the inner perimeter surface of the selective light-absorbing portion 118 in the light guide path 110 but passes through the selective light-absorbing portion 118 to reach the light-receiving element PD. That is, in the third embodiment, the depth of field of the visible light can be made greater than the depth of field of the near-infrared light, so that the detection of the fingerprint using the visible light and the detection of the vascular pattern using the near-infrared light can be appropriately performed.

(Modification)

Figure 21:
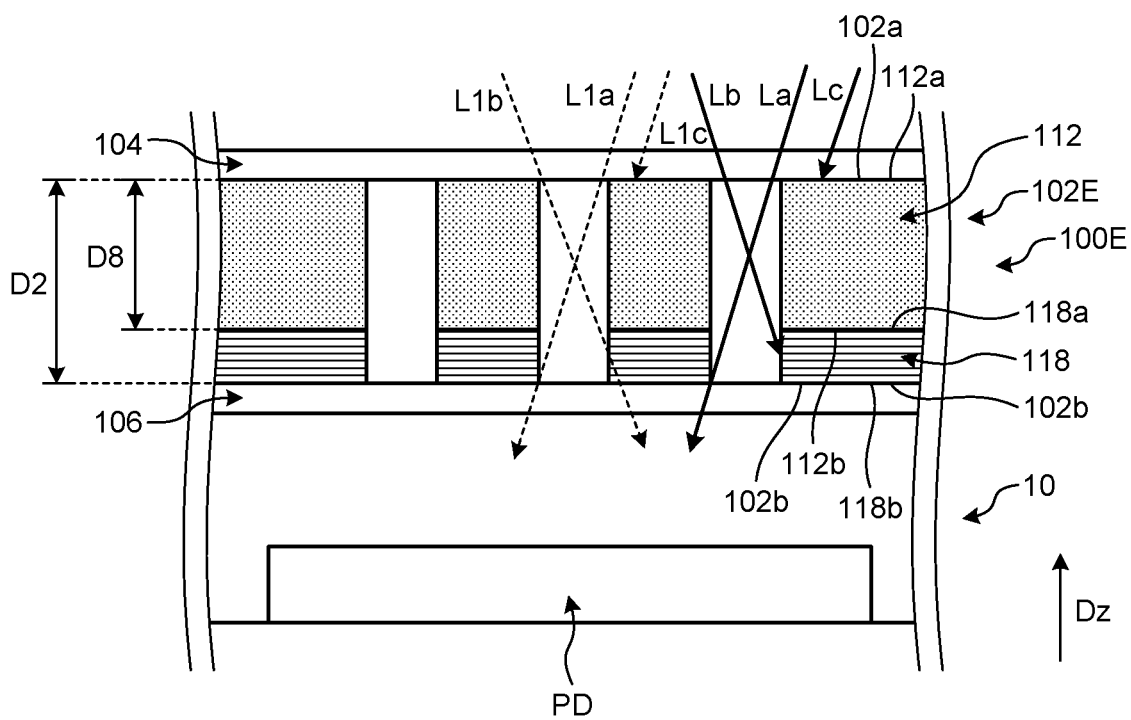
FIG. 21 is a schematic diagram of the light guide body according to a modification.

The following describes a modification of the third embodiment. FIG. 21 is a schematic diagram of the light guide body according to the modification. In the third embodiment, the selective light-absorbing portion 118 surrounds the periphery of the light guide path 110, and the light-absorbing portion 112 surrounds the periphery of the selective light-absorbing portion 118. However, the structure of the light guide path 110, the selective light-absorbing portion 118, and the light-absorbing portion 112 is not limited to such a configuration. For example, as illustrated in the modification of FIG. 21, the selective light-absorbing portion 118 surrounds the periphery of the light guide path 110, but does not surround the entire area in the third direction Dz of the light guide path 110, and surrounds only a partial area in the third direction Dz of the light guide paths 110. That is, the surface 118b on the lower side of the selective light-absorbing portion 118 is located at the same position as the surface 102b of the light guide portion 102, but the surface 118a on the upper side of the selective light-absorbing portion 118 is located on the surface 102b side, this is, on the lower side than the surface 102a of the light guide portion 102. The selective light-absorbing portion 118 surrounds the periphery of the light guide path 110 in an area from the surface 118a to the surface 118b.

The light-absorbing portion 112 is provided on the surface 112a of the selective light-absorbing portion 118 and surrounds the periphery of the light guide path 110. The surface 112b on the lower side of the light-absorbing portion 112 contacts the surface 118a of the selective light-absorbing portion 118, and the surface 112a on the upper side of the light-absorbing portion 112 is located at the same position as the surface 102a of the light guide portion 102. The light-absorbing portion 112 surrounds the periphery of the light guide path 110 in an area from the surface 112a to the surface 112b. A length D8 in the third direction Dz of the light-absorbing portion 112 is preferably 0.2 to 1.0 times the length D2 in third direction Dz of the light guide path 110.

As described above, also in the configuration of FIG. 21, the light Lb of the visible light having a smaller incident angle (having a smaller incident angle with respect to the surface 102a) than that of the light La of the visible light is incident on the inner perimeter surface of the selective light-absorbing portion 118 in the light guide path 110 and is absorbed by the selective light-absorbing portion 118 so as to be restrained from reaching the light-receiving element PD. In contrast, the light L1b of the near-infrared light having a smaller incident angle than that of the light L1a of the near-infrared light is incident on the inner perimeter surface of the selective light-absorbing portion 118 in the light guide path 110 but passes through the selective light-absorbing portion 118 to reach the light-receiving element PD. That is, also in this case, the depth of field of the visible light can be made larger than the depth of field of the near-infrared light, so that the detection of the fingerprint using the visible light and the detection of the vascular pattern using the near-infrared light can be appropriately performed.

Other operational advantages accruing from the aspects described in the embodiments that are obvious from the description of the present specification, or that are conceivable as appropriate by those skilled in the art will naturally be understood as accruing from the present invention.

What is claimed is:

1. A detection device comprising:
   a plurality of light-receiving elements configured to receive light; and
   a light guide portion having one surface that faces the light-receiving elements, wherein
   the light guide portion comprises a plurality of light guide paths provided throughout from the one surface to an other surface of the light guide portion, and a light-absorbing portion having higher absorbance of the light than that of the light guide paths,
   when viewed from a direction in which the light-receiving elements and the light guide portion are stacked, more than one of the light guide paths overlap one of the light-receiving elements, and
   the light-absorbing portion comprises a first light-absorbing portion configured to absorb visible light but transmit infrared light, and a second light-absorbing portion configured to absorb visible light and infrared light.

2. The detection device according to claim 1, wherein each of the light guide paths is formed of a solid member having higher light transmittance than that of the light-absorbing portion.

3. The detection device according to claim 1, wherein the light guide paths overlapping the one light-receiving element have aspect ratios different from one another, the aspect ratios being ratios of lengths from the one surface to the other surface to diameters of the respective light guide paths.

4. The detection device according to claim 1, wherein the light guide paths have diameters decreasing toward the other surface.

5. The detection device according to claim 1, wherein the light guide portion further comprises low-refractive-index portions having a lower light refractive index than that of the light guide paths.

6. The detection device according to claim 5, wherein the low-refractive-index portions surround peripheries of the respective light guide paths, and the light-absorbing portion surrounds a periphery of each of the low-refractive-index portions.

7. The detection device according to claim 5, wherein the low-refractive-index portions surround peripheries of the respective light guide paths, and the light-absorbing portion is provided on an other surface side of the low-refractive-index portions.

8. The detection device according to claim 1, wherein the light guide portion is formed of an organic material.

9. A method for manufacturing a detection device, the detection device comprising a plurality of light-receiving elements configured to receive light and a light guide portion having one surface that faces the light-receiving elements, wherein the light guide portion comprises a plurality of light guide paths provided throughout from the one surface to an other surface of the light guide portion, and a light-absorbing portion having higher absorbance of the light than that of the light guide paths, when viewed from a direction in which the light-receiving elements and the light guide portion are stacked, more than one of the light guide paths overlap one of the light-receiving elements, and the light guide portion is formed of an organic material, the method comprising:
   applying a first organic material onto a substrate;
   emitting light to an area of the first organic material applied onto the substrate where the light guide paths are to be formed, and curing the first organic material in the area irradiated with the light to form the light guide paths made of the cured first organic material;
   removing uncured first organic material from the substrate;
   applying a second organic material to an area on the substrate where the light guide paths are not formed; and
   forming the light-absorbing portion by emitting light or heat to the second organic material on the substrate and curing the second organic material.

* * * * *